United States Patent
de Juan, Jr. et al.

(10) Patent No.: US 11,141,312 B2
(45) Date of Patent: Oct. 12, 2021

(54) LACRIMAL IMPLANT DETECTION

(71) Applicant: Mati Therapeutics Inc., Austin, TX (US)

(72) Inventors: Eugene de Juan, Jr., San Francisco, CA (US); Stephen Boyd, Murrieta, CA (US); Cary J. Reich, Los Gatos, CA (US); Christopher V. Cardenas, Redwood City, CA (US); Tommy Jewell, Albuquerque, NM (US); Lorrie Ma, San Jose, CA (US); Tuan Nguyen, San Jose, CA (US)

(73) Assignee: Mati Therapeutics Inc., Austin, TX (US)

( * ) Notice: Subject to any disclaimer, the term of this patent is extended or adjusted under 35 U.S.C. 154(b) by 250 days.

(21) Appl. No.: 14/690,874

(22) Filed: Apr. 20, 2015

(65) Prior Publication Data

US 2015/0374541 A1 Dec. 31, 2015

Related U.S. Application Data

(63) Continuation of application No. 12/231,987, filed on Sep. 5, 2008, now Pat. No. 9,011,361.
(Continued)

(51) Int. Cl.
*A61F 9/00* (2006.01)
*A61B 5/06* (2006.01)
(Continued)

(52) U.S. Cl.
CPC .............. *A61F 9/0017* (2013.01); *A61B 5/06* (2013.01); *A61B 5/411* (2013.01);
(Continued)

(58) Field of Classification Search
CPC ................ A61F 9/0017; A61F 9/00772; A61F 2250/0068; A61F 2250/0096;
(Continued)

(56) References Cited

U.S. PATENT DOCUMENTS

| 3,828,777 A | 8/1974 | Ness |
| 3,865,108 A | 2/1975 | Hartop |

(Continued)

FOREIGN PATENT DOCUMENTS

| AU | 2002/3644336 | 7/2003 |
| EP | 0442745 | 8/1991 |

(Continued)

OTHER PUBLICATIONS

De Juan, Jr., E et al., "Drug Delivery Implants for Inhibition of Optical Defects", U.S. Appl. No. 60/871,867, filed Dec. 26, 2006, 59 pgs.

(Continued)

*Primary Examiner* — Philip R Wiest
(74) *Attorney, Agent, or Firm* — Koren Anderson

(57) ABSTRACT

This document discusses, among other things, an apparatus comprising a lacrimal implant insertable at least partially into a lacrimal punctum. The lacrimal implant comprises an implant core, and an implant body. The implant body includes a cavity sized and shaped to receive the implant core. At least one of the implant core and the implant cavity includes a detection device configured to allow automatic detection of the lacrimal implant with a separate detector device.

46 Claims, 25 Drawing Sheets

Related U.S. Application Data

(60) Provisional application No. 61/050,901, filed on May 6, 2008, provisional application No. 60/970,807, filed on Sep. 7, 2007.

(51) Int. Cl.

| | |
|---|---|
| *A61B 5/00* | (2006.01) |
| *G01R 33/02* | (2006.01) |
| *G01R 33/07* | (2006.01) |
| *A61F 9/007* | (2006.01) |
| *A61L 31/04* | (2006.01) |
| *A61L 31/06* | (2006.01) |
| *A61L 31/14* | (2006.01) |
| *A61L 31/16* | (2006.01) |
| *A61B 8/08* | (2006.01) |

(52) U.S. Cl.
CPC ........ *A61F 9/00772* (2013.01); *A61L 31/043* (2013.01); *A61L 31/044* (2013.01); *A61L 31/06* (2013.01); *A61L 31/145* (2013.01); *A61L 31/16* (2013.01); *G01R 33/0213* (2013.01); *G01R 33/072* (2013.01); *A61B 5/0031* (2013.01); *A61B 8/0833* (2013.01); *A61B 2562/08* (2013.01); *A61F 2250/0068* (2013.01); *A61F 2250/0096* (2013.01); *A61L 2300/404* (2013.01); *A61L 2300/43* (2013.01)

(58) Field of Classification Search
CPC ...... A61L 31/043; A61L 31/044; A61L 31/16; A61L 31/145; A61L 31/06; A61L 2300/404; A61L 2300/43; A61B 5/06; A61B 5/411; A61B 5/0031; G01R 33/0213; G01R 33/072
USPC ........... 604/8, 104, 171, 246, 294, 514, 521, 604/891.1, 93.01
See application file for complete search history.

(56) References Cited

U.S. PATENT DOCUMENTS

| | | | |
|---|---|---|---|
| 3,949,750 A | 4/1976 | Freeman | |
| 4,014,335 A | 3/1977 | Arnold | |
| 4,281,654 A | 8/1981 | Shell | |
| 4,304,765 A | 12/1981 | Shell | |
| 4,540,408 A | 9/1985 | Lloyd | |
| 4,660,546 A | 4/1987 | Herrick | |
| 4,747,404 A | 5/1988 | Jampel | |
| 4,886,488 A | 12/1989 | White | |
| 4,915,684 A | 4/1990 | MacKeen | |
| 4,959,048 A | 9/1990 | Seder | |
| 5,041,081 A | 8/1991 | Odrich | |
| 5,049,142 A | 9/1991 | Herrick | |
| 5,053,030 A | 10/1991 | Herrick | |
| 5,098,443 A | 3/1992 | Parel | |
| 5,116,371 A | 5/1992 | Christensen | |
| 5,128,058 A | 7/1992 | Ishii | |
| 5,133,159 A | 7/1992 | Nelson | |
| 5,143,724 A | 9/1992 | Leshchiner | |
| 5,163,959 A | 11/1992 | Herrick | |
| 5,171,270 A | 12/1992 | Herrick | |
| 5,178,635 A * | 1/1993 | Gwon .................. A61F 9/0017 250/302 |
| 5,283,063 A | 2/1994 | Freeman | |
| 5,300,114 A | 4/1994 | Gwon | |
| 5,318,513 A | 6/1994 | Leib | |
| 5,322,691 A | 6/1994 | Darougar | |
| 5,334,137 A | 8/1994 | Freeman | |
| 5,366,739 A | 11/1994 | MacKenn | |
| 5,395,618 A | 3/1995 | Darougar | |
| 5,417,651 A | 5/1995 | Guena | |
| 5,423,777 A | 6/1995 | Tajiri | |
| 5,443,505 A | 8/1995 | Wong | |
| 5,466,233 A | 11/1995 | Weiner | |
| 5,514,379 A | 5/1996 | Weissleder | |
| 5,556,633 A | 9/1996 | Haddad | |
| 5,707,643 A | 1/1998 | Ogura | |
| 5,723,005 A | 3/1998 | Herrick | |
| 5,739,176 A * | 4/1998 | Dunn .................. A61L 26/0076 523/113 |
| 5,741,292 A | 4/1998 | Mendius | |
| 5,766,243 A | 6/1998 | Christensen | |
| 5,770,589 A | 6/1998 | Billson | |
| 5,773,019 A * | 6/1998 | Ashton .................. A61P 27/00 424/423 |
| 5,824,048 A | 10/1998 | Tuch | |
| 5,824,073 A | 10/1998 | Peyman | |
| 5,826,584 A | 10/1998 | Schmitt | |
| 5,830,171 A | 11/1998 | Wallace | |
| 5,840,054 A | 11/1998 | Hamano | |
| 5,947,974 A | 9/1999 | Brady | |
| 5,961,370 A | 10/1999 | Valle | |
| 5,962,383 A | 10/1999 | Doyel | |
| 5,993,407 A | 11/1999 | Moazed | |
| 6,010,391 A | 1/2000 | Lewellen | |
| 6,016,806 A | 1/2000 | Webb | |
| 6,027,470 A | 2/2000 | Mendius | |
| 6,041,785 A | 3/2000 | Webb | |
| 6,082,362 A | 7/2000 | Webb | |
| 6,095,901 A | 8/2000 | Robinson | |
| 6,117,441 A | 9/2000 | Moo-Young | |
| 6,149,684 A | 11/2000 | Herrick | |
| 6,196,993 B1 | 3/2001 | Cohan | |
| 6,217,895 B1 * | 4/2001 | Guo .................. A61K 9/0051 424/427 |
| 6,224,630 B1 | 5/2001 | Bao | |
| 6,234,175 B1 | 5/2001 | Zhou | |
| 6,238,363 B1 | 5/2001 | Kurihashi | |
| 6,254,562 B1 | 7/2001 | Fouere | |
| 6,264,971 B1 | 7/2001 | Darougar | |
| 6,290,684 B1 | 9/2001 | Herrick | |
| 6,306,114 B1 | 10/2001 | Freeman | |
| 6,331,313 B1 | 12/2001 | Wong | |
| 6,344,047 B1 | 2/2002 | Price | |
| 6,371,122 B1 | 4/2002 | Mandelkorn | |
| 6,375,972 B1 | 4/2002 | Guo | |
| 6,383,192 B1 | 5/2002 | Kurihashi | |
| 6,428,502 B1 | 8/2002 | Lang | |
| 6,441,047 B2 | 8/2002 | DeSantis, Jr. | |
| 6,455,062 B1 | 9/2002 | Olejnik | |
| 6,512,747 B1 | 1/2003 | Umeuchi | |
| 6,534,693 B2 | 3/2003 | Fischell | |
| 6,605,108 B2 | 8/2003 | Mendius | |
| 6,629,533 B1 | 10/2003 | Webb | |
| 6,645,963 B2 | 11/2003 | Higashiyama | |
| 6,646,001 B2 | 11/2003 | Hellberg | |
| 6,706,275 B1 | 3/2004 | Camp | |
| 6,729,939 B2 | 5/2004 | Wrue | |
| 6,756,049 B2 | 6/2004 | Brubaker | |
| 6,780,164 B2 | 8/2004 | Bergheim | |
| 6,840,931 B2 | 1/2005 | Peterson | |
| 6,846,318 B2 | 1/2005 | Camp | |
| 6,866,563 B2 | 3/2005 | Green | |
| 6,964,781 B2 | 11/2005 | Brubaker | |
| 6,982,090 B2 | 1/2006 | Gillespie | |
| 6,991,808 B2 | 1/2006 | Brubaker | |
| 6,994,684 B2 | 2/2006 | Murray | |
| 7,001,615 B1 | 2/2006 | Singh | |
| 7,017,580 B2 | 3/2006 | Prescott | |
| 7,117,870 B2 | 10/2006 | Prescott | |
| 7,135,009 B2 | 11/2006 | Tu | |
| 7,204,253 B2 | 4/2007 | Mendius | |
| 7,204,995 B2 | 4/2007 | El-Sherif | |
| 7,510,541 B2 | 3/2009 | Hanna | |
| 7,662,864 B2 | 2/2010 | Kanamathareddy | |
| 7,708,401 B2 | 5/2010 | Sabeta | |
| 7,752,519 B2 | 7/2010 | Yeo | |
| 7,986,633 B2 | 7/2011 | Ryu | |
| 7,998,497 B2 | 8/2011 | de Juan, Jr. | |
| 8,691,265 B2 | 4/2014 | de Juan | |
| 8,747,884 B2 | 6/2014 | de Juan, Jr. | |
| 8,795,711 B2 | 8/2014 | de Juan, Jr. | |

(56) References Cited

U.S. PATENT DOCUMENTS

| | | | |
|---|---|---|---|
| 9,011,361 B2* | 4/2015 | de Juan, Jr. | A61L 31/044 604/8 |
| 9,168,222 B2 | 10/2015 | de Juan, Jr. | |
| 2002/0028181 A1 | 3/2002 | Miller | |
| 2002/0032400 A1 | 3/2002 | Moazed | |
| 2002/0055701 A1 | 5/2002 | Fischell | |
| 2002/0103255 A1 | 8/2002 | Hellberg | |
| 2002/0111576 A1 | 8/2002 | Greene | |
| 2002/0151960 A1 | 10/2002 | Mendius | |
| 2002/0169409 A1* | 11/2002 | Gillespie | A61F 9/00772 604/20 |
| 2002/0193441 A1 | 12/2002 | Robertson | |
| 2002/0198453 A1 | 12/2002 | Herrick | |
| 2003/0095534 A1 | 5/2003 | Jiang | |
| 2003/0130612 A1 | 7/2003 | Moazed | |
| 2003/0139673 A1 | 7/2003 | Vivenzio | |
| 2003/0152522 A1 | 8/2003 | Miller | |
| 2004/0009222 A1 | 1/2004 | Chou | |
| 2004/0043067 A1 | 3/2004 | Salamone | |
| 2004/0071761 A1 | 4/2004 | Miller | |
| 2004/0081081 A1 | 4/2004 | Colombo | |
| 2004/0092435 A1 | 5/2004 | Peyman | |
| 2004/0100929 A1 | 5/2004 | Garcia-Luna-Aceves | |
| 2004/0102729 A1 | 5/2004 | Haffner | |
| 2004/0121014 A1 | 6/2004 | Guo | |
| 2004/0127843 A1 | 7/2004 | Tu | |
| 2004/0137068 A1 | 7/2004 | Bhushan | |
| 2004/0141151 A1 | 7/2004 | Gillespie | |
| 2004/0142902 A1* | 7/2004 | Struijker-Boudier | A61K 9/0024 514/53 |
| 2004/0144392 A1 | 7/2004 | Mueller | |
| 2004/0147870 A1 | 7/2004 | Burns | |
| 2004/0156345 A1 | 8/2004 | Steer | |
| 2004/0170685 A1 | 9/2004 | Carpenter | |
| 2004/0175410 A1 | 9/2004 | Ashton | |
| 2004/0176341 A1 | 9/2004 | Chou | |
| 2004/0185887 A1 | 9/2004 | Wolman | |
| 2004/0208910 A1 | 10/2004 | Ashton | |
| 2004/0210182 A1 | 10/2004 | Fouere | |
| 2004/0236343 A1 | 11/2004 | Taylor | |
| 2004/0249333 A1 | 12/2004 | Bergheim | |
| 2004/0254516 A1 | 12/2004 | Murray | |
| 2004/0265356 A1 | 12/2004 | Mosack | |
| 2005/0043412 A1 | 2/2005 | Ichikawa | |
| 2005/0048121 A1 | 3/2005 | East | |
| 2005/0095269 A1 | 5/2005 | Ainpour | |
| 2005/0107734 A1 | 5/2005 | Coroneo | |
| 2005/0129731 A1 | 6/2005 | Horres | |
| 2005/0192527 A1 | 9/2005 | Gharib | |
| 2005/0197614 A1 | 9/2005 | Pritchard et al. | |
| 2005/0220882 A1 | 10/2005 | Pritchard | |
| 2005/0232972 A1* | 10/2005 | Odrich | A61F 9/0017 424/427 |
| 2005/0244469 A1 | 11/2005 | Whitcup | |
| 2005/0255564 A1 | 11/2005 | Sakai | |
| 2005/0266047 A1 | 12/2005 | Tu | |
| 2005/0271704 A1 | 12/2005 | Tu | |
| 2005/0283109 A1 | 12/2005 | Peyman | |
| 2006/0013835 A1 | 1/2006 | Anderson | |
| 2006/0020248 A1 | 1/2006 | Prescott | |
| 2006/0020253 A1 | 1/2006 | Prescott | |
| 2006/0074370 A1 | 4/2006 | Zhou | |
| 2006/0100700 A1 | 5/2006 | Bernard | |
| 2006/0106352 A1 | 5/2006 | Kurihashi | |
| 2006/0122553 A1 | 6/2006 | Hanna | |
| 2007/0021762 A1 | 1/2007 | Liu | |
| 2007/0083146 A1 | 4/2007 | Murray | |
| 2007/0088444 A1 | 4/2007 | Hodorek | |
| 2007/0123924 A1 | 5/2007 | Becker | |
| 2007/0132125 A1 | 6/2007 | Rastogi | |
| 2007/0135914 A1 | 6/2007 | Herrick | |
| 2007/0243230 A1 | 10/2007 | de Juan | |
| 2007/0269487 A1* | 11/2007 | de Juan, Jr. | A61F 9/0017 424/427 |
| 2007/0298075 A1 | 12/2007 | Borgia | |
| 2007/0299515 A1 | 12/2007 | Herrick | |
| 2007/0299516 A1 | 12/2007 | Cui | |
| 2008/0038317 A1 | 2/2008 | Chang | |
| 2008/0045878 A1 | 2/2008 | Bergheim | |
| 2008/0045911 A1* | 2/2008 | Borgia | A61F 9/0017 604/294 |
| 2008/0097442 A1* | 4/2008 | Dixon | A61B 90/92 606/281 |
| 2008/0181930 A1 | 7/2008 | Rodstrom | |
| 2008/0299176 A1 | 12/2008 | Lai | |
| 2009/0092654 A1 | 4/2009 | de Juan, Jr. | |
| 2009/0099626 A1 | 4/2009 | de Juan, Jr. | |
| 2009/0104243 A1 | 4/2009 | Utkhede | |
| 2009/0104248 A1 | 4/2009 | Rapacki | |
| 2009/0105749 A1 | 4/2009 | de Juan | |
| 2009/0118702 A1 | 5/2009 | Lazar | |
| 2009/0122765 A1 | 5/2009 | Dimou | |
| 2009/0131959 A1 | 5/2009 | Rolland | |
| 2009/0252236 A1 | 10/2009 | Li | |
| 2009/0264861 A1 | 10/2009 | Jain | |
| 2009/0280158 A1 | 11/2009 | Butuner | |
| 2009/0298390 A1 | 12/2009 | Rapacki | |
| 2010/0021519 A1 | 1/2010 | Shenoy | |
| 2010/0034870 A1 | 2/2010 | Sim | |
| 2010/0040670 A1 | 2/2010 | Odrich | |
| 2010/0189766 A1 | 7/2010 | Utkhede | |
| 2010/0209477 A1 | 8/2010 | Butuner | |
| 2010/0274204 A1 | 10/2010 | Rapacki | |
| 2010/0274224 A1 | 10/2010 | Jain | |
| 2014/0161863 A1 | 6/2014 | de Juan, Jr. | |
| 2017/0304194 A1* | 10/2017 | Utkhede, Jr. | A61F 9/0017 |

FOREIGN PATENT DOCUMENTS

| | | |
|---|---|---|
| EP | 0621022 | 7/1999 |
| EP | 098844 A2 | 3/2000 |
| GB | 2216795 | 10/1989 |
| JP | 7178130 | 7/1995 |
| JP | 10033584 | 2/1998 |
| JP | 11505159 | 5/1999 |
| JP | 2004202276 | 7/2004 |
| JP | 2005000628 | 1/2005 |
| JP | 2005058622 | 3/2005 |
| JP | 2005110765 | 4/2005 |
| JP | 2005110930 | 4/2005 |
| JP | 2005312835 | 11/2005 |
| JP | 2005319190 | 11/2005 |
| JP | 2005328922 | 12/2005 |
| JP | 2007195819 | 8/2007 |
| NZ | 581461 | 4/2011 |
| WO | WO-93012765 | 7/1993 |
| WO | WO-96005544 | 2/1996 |
| WO | WO-98033461 | 8/1998 |
| WO | WO-98042282 | 10/1998 |
| WO | WO-99037260 | 7/1999 |
| WO | WO-99044553 | 9/1999 |
| WO | WO-99064089 | 12/1999 |
| WO | WO-99065544 | 12/1999 |
| WO | WO-00003705 | 1/2000 |
| WO | WO-00027321 | 5/2000 |
| WO | WO-00062760 | 10/2000 |
| WO | WO-01080825 | 11/2001 |
| WO | WO-02011783 | 2/2002 |
| WO | WO-02058667 | 8/2002 |
| WO | WO-02083198 | 10/2002 |
| WO | WO-03017897 | 3/2003 |
| WO | WO-03022242 | 3/2003 |
| WO | WO-03057101 | 7/2003 |
| WO | WO-2004004614 | 1/2004 |
| WO | WO-2004024043 | 3/2004 |
| WO | WO-2004105658 | 12/2004 |
| WO | WO-2004112639 | 12/2004 |
| WO | WO-2005000154 | 1/2005 |
| WO | WO-2005051234 | 6/2005 |
| WO | WO-2005060210 | 6/2005 |
| WO | WO-2005086694 | 9/2005 |

(56) References Cited

FOREIGN PATENT DOCUMENTS

| WO | WO-2006014434 | 2/2006 |
|---|---|---|
| WO | WO-2006014793 | 2/2006 |
| WO | WO-2006031658 | 3/2006 |
| WO | WO-2006044669 | 4/2006 |
| WO | WO-2006057859 | 6/2006 |
| WO | WO-2006096586 | 9/2006 |
| WO | WO-2006122414 | 11/2006 |
| WO | WO-2007008262 | 1/2007 |
| WO | WO-20071 15261 | 10/2007 |
| WO | WO-2007115259 | 10/2007 |
| WO | WO-20071 49771 | 12/2007 |
| WO | WO-20071 49832 | 12/2007 |
| WO | WO-2008056060 | 5/2008 |
| WO | WO-2008094989 | 8/2008 |
| WO | WO-2009032328 | 3/2009 |
| WO | WO-2009035562 | 3/2009 |
| WO | WO-2009035565 | 3/2009 |
| WO | WO-2010008883 | 1/2010 |
| WO | WO-201 0096822 | 8/2010 |
| WO | WO-201 0085696 | 6/2011 |

OTHER PUBLICATIONS

De Juan, Jr., E et al., "Insertion and Extraction Tools for Punctal Implants", U.S. Appl. No. 60/970,840, filed Sep. 7, 2007, 29 pgs.
De Juan, Jr., E et al., "Multiple Drug Delivery Systems and Combinations of Drugs With Punctal Implants", U.S. Appl. No. 60/970,820, filed Sep. 7, 2007, 67 pgs.
De Juan, Jr., E et al., "System and Methods for Detection of Nasolcrimal Devices", U.S. Appl. No. 60/970,807, filed Sep. 7, 2007, 44 pgs.
"European Application No. 08830451.4, Examination Report dated Nov. 5, 2010".
"International Application Serial No. PCT/US2008/010479, International Search Report dated Dec. 15, 2008", 5 pgs.
"International Application Serial No. PCT/US2008/010479, Written Opinion dated Dec. 15, 2008", 7 pgs.
"International Application Serial No. PCT/US2008/010487, International Search Report dated May 25, 2009", 5 pgs.
"International Application Serial No. PCT/US2008/010497, International Search Report dated Mar. 6, 2009".
"International Application Serial No. PCT/US2008/010497, Written Opinion dated Mar. 6, 2009".
"International Application Serial No. PCT/US2008/010502, International Search Report dated Mar. 5, 2009", 7 pgs.
"International Application Serial No. PCT/US2008010502, Written Opinion dated Mar. 5, 2009", 9 pgs.
Lazar, E et al., "Treatment Medium Delivery Device and Methods for Delivery of Such Treatment Mediums to the Eye Using Such a Delivery Device", U.S. Appl. No. 11/571,147, filed Dec. 21, 2006, 33 pgs.
"Quantum Dot Nanomaterials For Research Specification Sheet", © 2006 Evident Technologies, Inc, (2006), 6 pgs.
Reich, C et al., "Nasolacriminal Drainage System Implants for Drug Delivery", U.S. Appl. No. 60/970,709, filed Sep. 7, 2007, 103 pgs.
"Russian Application Serial No. 2010112426, Official Action dated Jun. 7, 2012", 15 pgs.
"Australian Application Serial No. 2007234445, Examiner Report dated Oct. 12, 2009", 2 pgs.
"International Application Serial No. PCT/US2008/010487, Written Opinion dated May 25, 2009", 8 pgs.
"Canadian Application Serial No. 2,648,066, Office Action dated Nov. 1, 2010".
"Oasis Product Catalog", 7 pgs.
"International Application Serial No. PCT/US07/65792, International Search Report dated Nov. 20, 2008", 2 pgs.
"U.S. Appl. No. 12/604,202, Preliminary Amendment filed Nov. 30, 2009", 6 pgs.
"U.S. Appl. No. 10/825,047, Response filed Aug. 18, 2008 to Restriction Requirement dated Jul. 17, 2008", 10 pgs.
"U.S. Appl. No. 11/695,537, Notice dated Nov. 28, 2008 Regarding a Noncompliant or Nonresponsive Amendment filed on Nov. 3, 2008", 3 pgs.
"New Zealand Application Serial No. 588938, Examination Report dated Apr. 26, 2012".
"Korean Application Serial No. 10-2008-7026758, Office Action dated Oct. 25, 2010".
"Production Information for EaglePlug(r) TearFlow tm", 1 pg.
"International Application Serial No. PCT/US07/65792, International Written Opinion dated Nov. 20, 2008", 5 pgs.
"U.S. Appl. No. 11/695,545, Preliminary Amendment and Response filed Nov. 6, 2008 to Restriction Requirement dated Oct. 6, 2008", 14 pgs.
"Chinese Application Serial No. 200580028979.2, First Office Action dated Dec. 12, 2008", 7 pgs.
"U.S. Appl. No. 10/825,047, Restriction Requirement dated Jul. 17, 2008", 6 pgs.
"U.S. Appl. No. 11/695,537, Restriction Requirement dated Oct. 3, 2008", 10 pgs.
"Israeli Application Serial No. 212114, Notice of Defects dated Sep. 12, 2011".
"Korean Application Serial No. 10-2008-7026781, Office Action dated Aug. 26, 2010".
"Production Information for the Micro Flow™ Punctal Occluder", 1 pg.
"International Application Serial No. PCT/US2007/065789, International Search Report dated Aug. 13, 2008", 3 pgs.
"U.S. Appl. No. 10/825,047, Final Office Action dated Jun. 9, 2009", 14 pgs.
"U.S. Appl. No. 11/571,147, Restriction Requirement dated Jun. 26, 2009", 5 pgs.
"New Zealand Application Serial No. 571758, Examination Report dated Nov. 14, 2011".
"U.S. Appl. No. 11/695,537, Response filed Nov. 3, 2008 to Restriction Requirement dated Oct. 3, 2008", 15 pgs.
"Israeli Application Serial No. 194514, Notice of Defects dated Sep. 12, 2011".
"New Zealand Application Serial No. 571758, Examination Report dated May 24, 2010", 2 pgs.
"European Application Serial No. 05768122.3, Supplementary European Search Report dated Mar. 31, 2009", 3 pgs.
"U.S. Appl. No. 11/695,537, Non Final Office Action dated Sep. 18, 2009", 12 pgs.
"International Application Serial No. PCT/US2007/065789, Written Opinion dated Aug. 13, 2008", 5 pgs.
"U.S. Appl. No. 10/825,047, Response filed Apr. 22, 2009 to Non Final Office Action dated Oct. 22, 2008", 17 pgs.
"European Application Serial No. 05768122.3, Office Action dated Apr. 17, 2009", 6 pgs.
"Japanese Application Serial No. 2009-503335, Decision of Rejection dated Apr. 3, 2012".
"U.S. Appl. No. 11/695,537, Response filed Dec. 17, 2008 to Office Communication dated Nov. 28, 2008", 8 pgs.
"Japanese Application Serial No. 2009-503334, Notice of Rejection dated Aug. 30, 2011".
"U.S. Appl. No. 10/825,047, Non-Final Office Action dated Oct. 22, 2008, Other Description Mar. 4, 2015", 13 pgs.
"Australian Application Serial No. 2007234447, Examiner Report dated Oct. 6, 2009", 3 pgs.
"Chinese Application Serial No. 200780017166.2, Second Office Action dated Mar. 6, 2012".
"U.S. Appl. No. 11/695,545, Restriction Requirement dated Oct. 6, 2008", 10 pgs.
"U.S. Appl. No. 10/825,047, Response filed Oct. 22, 2009 to Final Office Action dated Jun. 9, 2009", 20 pgs.
"Korean Application No. 10/2006-0020490, Office Action dated Jul. 18, 2012", 4 pgs.
"Size Variation of the Lacrimal Punctum in Adults", 231-233.
"Time Release Ophthalmic Drug Delivery Insert", 1 pg.
"Manufacture of Expandable Nasolacrimal Drainage System Implants", 57 pgs.
"Expandable Nasolacrimal Drainage System Implants ", 82 pgs.

(56) References Cited

OTHER PUBLICATIONS

"Influence of Benzalkonium Chloride on the Penetration of Latanoprost into Rabbit Aqueous Humor After Ocular Instillations , Other Description Mar. 4, 2015", 1 pg.

"Permeability of Chemical Delivery Systems Across Rabbit Corneal (SIRC) Cell Line and Isolated Corneas: A Comparative Study, Other Description Mar. 4, 2015", 1 pg.

"Chapter 25—Ocular Penetration Enhancers", 527-548.

"Assessment of Drug Concentrations in Tears in Therapeutic Drug Monitoring: I. Determination of Valproic Acid in Tears by Gas Chromatography/Mass Spectrometry With EC/NCI Mode", 716-722.

"Controlled Release Veterinary Drug Delivery", 118 pgs.

"Manufacture of Drug Cores for Sustained Release of Therapeutic Agents", 66 pgs.

"Application Serial No. 15/405,991, Non-Final Office Action dated Apr. 6, 2017", 10 pgs.

"U.S. Appl. No. 15/405,991, Response Filed Aug. 7, 2017 to Non-Final Office Action dated Apr. 6, 2017", 6 pgs.

"U.S. Appl. No. 15/405,991, Notice of Allowance dated Aug. 23, 2017".

Final Written Decision in IPR 2019-00448 U.S. Pat. No. 9,849,082; dated Jun. 18, 2020.

\* cited by examiner

IMPLANT ID 1234 ID SIGNAL INFO, LATANOPROST, MANUFACTURE DATE, SHELF LIFE, ELUTION LIFE, IMPLANT DATE, PATIENT ID...

IMPLANT ID 1235 ID SIGNAL INFO, BIMATAPROST, MANUFACTURE DATE, SHELF LIFE, ELUTION LIFE, IMPLANT DATE, PATIENT ID...

IMPLANT ID 1236 ID SIGNAL INFO, BIMATAPROST, MANUFACTURE DATE, SHELF LIFE, ELUTION LIFE, IMPLANT DATE, PATIENT ID...

LACRIMAL IMPLANT DETECTION

CLAIM OF PRIORITY

This non-provisional application claims the benefit of priority under 35 U.S.C. § 119(e) to U.S. Provisional Patent Application Ser. No. 60/970,807 filed on Sep. 7, 2007, and to U.S. Provisional Patent Application Ser. No. 61/050,901 filed on May 6, 2008, the specifications of which are herein incorporated by reference in their entirety.

BACKGROUND OF THE INVENTION

The present application is related generally to implants for use in people and/or animals, and more specifically to detection of implants in or near the nasolacrimal drainage system, which are sometimes referred to as lacrimal implants.

A variety of challenges face patients and physicians in the area of eye therapy or treatment. In some instances, it may be desirable to plug one or more of the punctal ducts with an implant to alleviate eye problems, for example dry eye. In some instances, it may be desirable to also include a therapeutic agent with the implant that is capable of delivery of therapeutic treatment to the patient over a period of time.

Some of the problems associated with lacrimal implants, such as punctal or punctum plugs, are that they are very small and made of clear or skin colored silicone materials, making them difficult to see or detect. The lacrimal implants are also easily dislodged by the patient rubbing the eyes and the patient may not even know that the insert is missing, thus losing out on any treatment or therapeutic benefit the implant may provide. Another problem associated with therapeutic implants is that the patient does not know when delivery of the therapeutic agent is complete.

Implants having drugs may also be used for treatments other than the eye. For example, drug implants may be used for systemic treatment for cancer, HIV, diabetes, or specific location treatment of joints and tumors. Once implanted, it is difficult to tell if the implant has moved or shifted from the implant site, a problem for specific treatment locations. In addition, it is difficult to determine what drugs or therapies are used with the implant. For example, a patient with an implant may forget what drugs are in the implant, which may interact with other drugs.

In light of the above, it would be desirable to provide improved detection of implants that overcome at least some of the above mentioned shortcomings.

EXEMPLARY ASPECTS AND FEATURES OF THE INVENTION

The present invention is directed generally to the treatment of tissue, and more specifically the eye, with implants that include a detection device. In addition, the implant may also be a therapeutic implant that releases a therapeutic agent to treat the eye.

1. An apparatus includes includes a lacrimal implant insertable at least partially into a lacrimal punctum. The lacrimal implant includes an implant core and an implant body. The implant body includes a cavity sized and shaped to receive the implant core, and at least one of the implant core and the implant cavity includes a detection device that allows automatic detection of the lacrimal implant with a separate detector device.
2. The apparatus according to aspect 1, wherein the detection device optionally includes a radio frequency identifier (RFID) chip configured to communicate a detection signal to the detector device.
3. The apparatus according to aspects 1 and 2, wherein the detection device optionally includes a luminescent material configured to reflect light to the detector device.
4. The apparatus according to aspects 1-3, wherein the luminescent material optionally includes a quantum dot.
5. The apparatus according to aspects 1-4, wherein the detection device optionally includes an ultrasonically reflective material configured to reflect ultrasonic energy to the detector device.
6. The apparatus according to aspects 1-5, wherein the detection device of embodiments 1-6 optionally includes a magnetic material to retain a magnetic field detectable by the detector device. The magnetic material comprises at least one of magnetite, a metallic powder, a metallic ring, and a carbon powder.
7. The apparatus according to aspects 1-6, wherein the detection device of embodiments 1-6 optionally includes a magnetic material to retain a magnetic field detectable by the detector device.
8. The apparatus according to aspects 1-7, wherein the detection device optionally includes an electrically conductive material configured to cause a change in a characteristic impedance of a sensing circuit of the detector device due to proximity of the lacrimal implant to the sensing circuit.
9. The apparatus according to aspects 1-8, wherein the detection device optionally includes at least one of an optical contrast material and a color material in at least one of the implant core and the implant cavity configured to optically distinguish the lacrimal implant from a region of an eye.
10. The apparatus of according to aspects 1-9, wherein the detection device optionally includes a material visible when illuminated with an ultraviolet light source.
11. The apparatus according to aspects 1-10, wherein the implant core optionally includes a sustained release ocular agent.
12. The apparatus according to aspects 1-11, wherein the implant core optionally includes a sheath to house the agent. The detection device is disposed within the sheath.
13. The apparatus according to aspects 1-12, wherein a biocompatible material of the implant body optionally includes an agent for sustained release into an eye.
14. The apparatus according to aspects 1-13, wherein, the lacrimal implant optionally includes a polymeric coating on the outer surface of the implant body, and wherein polymeric coating includes the agent.
15. A method includes forming a lacrimal implant of biocompatible material, forming a cavity within a body of the lacrimal implant, providing an implant core within the cavity, wherein the implant core is sized and configured to provide sustained release of an agent into an eye, and providing a detection device in at least one of the implant core and the implant cavity, wherein the detection device is configured to allow automatic detection of the lacrimal implant with a separate detector device.
16. The method according to aspect 15, wherein the providing a detection device optionally includes providing at least one of an RFID chip configured to communicate a detection signal to the detector device, a luminescent material configured to reflect light to the detector device, an ultrasonically reflective material configured to reflect ultrasonic energy to the detector device, a ferromagnetic material capable of retaining a ferromagnetic property detectable by the detector device after application and removal of an external magnetic field, an electrically conductive material configured to cause a change in a characteristic impedance of a sensing circuit of the detector device, an optical contrast material configured to optically distinguish the punctum lug from a region of an eye, a color material to optically distinguish the lacrimal implant from a region of the eye, and a material visible when illuminated with an ultraviolet light source.

17. The method according to aspects 15 and 16, wherein the providing a detection device optionally includes providing the luminescent material, and the luminescent material optionally includes a quantum dot.

18. The method according to aspects 15-17, wherein the providing a detection device of embodiments 15-17 optionally includes providing the ferromagnetic material. The ferromagnetic material includes at least one of magnetite, a metallic powder, a metallic ring, and a carbon powder.

19. The method according to aspects 15-18, wherein the providing a detection device optionally includes providing a luminescent material configured to reflect light to the detector device. The method optionally includes exposing the lacrimal implant to incident light of a first wavelength range using a light emitting source, detecting light of a second wavelength range at a detection device, wherein the received light is reflected off of the lacrimal implant, and providing an indication when sufficient reflected light is detected to indicate proximity of a lacrimal implant.

20. The method according to aspect 19, wherein the first wavelength range of embodiment 19 optionally includes a blue spectrum, and the second wavelength range optionally includes a green spectrum.

21. The method according to aspects 19 and 20, wherein the exposing the lacrimal implant to incident light optionally includes exposing the lacrimal implant to incident light of a first wavelength range of an infrared spectrum, and the detecting light includes detecting light of a second wavelength range of the infrared spectrum.

22. The method according to aspects 19-21, wherein the providing an indication of embodiments 19-21 optionally includes providing an audible indication.

23. The method according to aspects 19-22, wherein the providing an indication optionally includes providing a visual indication.

24. A method of treating an eye disorder includes inserting a lacrimal implant into at least one lacrimal punctum of the subject and detecting the detection device of the lacrimal implant with the separate detector device. The lacrimal implant includes an implant body of biocompatible material, wherein the implant body includes a cavity extending inward into the implant body from an end of the implant body, an implant core sized and configured to provide sustained release of an agent into an eye, wherein the implant core is carried within the cavity of the implant body, and wherein at least one of the implant core and the implant cavity includes a detection device configured to allow automatic detection of the lacrimal implant with a separate detector device, and a supply of the agent disposed in the implant core, the supply configured to provide the sustained release of the agent.

25. The method according to aspect 24, wherein the agent optionally includes an agent to treat a glaucoma disease.

26. The method according to aspects 24 and 25, wherein the agent optionally includes an agent to treat at least one of ocular hypertension or primary open angle glaucoma.

27. An apparatus includes a lacrimal implant insertable at least partially into a lacrimal punctum. The lacrimal implant includes an implant body of biocompatible material. The implant body includes a detection device configured to allow detection of the lacrimal implant and to identify at least one attribute of the lacrimal implant.

28. The apparatus according to aspect 27, wherein the detection device optionally includes a radio frequency identifier (RFID) chip to communicate attribute information to a separate detector device.

29. The apparatus according to aspects 27 and 28, wherein the detection device optionally includes a color in the lacrimal implant. The color identifies the attribute of the lacrimal implant.

30. The apparatus according to aspects 27-29, wherein the detection device optionally includes a luminescent material, and the luminescent material reflects the color.

31. The apparatus according to aspects 27-30, wherein the luminescent material of embodiments 27-30 optionally includes a quantum dot.

32. The apparatus according to aspects 27-31, wherein the detection device optionally includes a material visible with an ultraviolet light source, and the detection device identifies the attribute when illuminated with the ultraviolet light source.

33. The apparatus according to aspects 27-32, wherein the detection device optionally includes a material elutable by the lacrimal implant and a bio-erodable surface. The bio-erodable surface elutes the material to identify the attribute.

34. The apparatus according to aspects 27-33, wherein the lacrimal implant optionally has a sustained release ocular agent, and the attribute of the lacrimal implant includes at least one of a type of the ocular agent, a dose of the ocular agent, and an indication of when release of the ocular agent is complete.

35. The apparatus according to aspects 27-34, wherein the identifiable attribute optionally includes at least one of the lacrimal implant manufacturer, the lacrimal implant manufacturer's lot number, a date the lacrimal implant was implanted, an expiration date of the implant, an indication of a location of where the lacrimal implant was implanted, an indication to identify a physician, and an indication to identify a patient.

36. A method includes forming a lacrimal implant of biocompatible material, wherein the punctum plug includes an implant body, and disposing a detection device in the implant body wherein the detection device is configured to allow detection of the lacrimal implant and to identify at least one attribute of the lacrimal implant.

37. The method according to aspect 36, wherein the disposing a detection device of embodiment 36 optionally includes at least one of an RFID chip configured to communicate attribute information to a separate detector device, a color in the lacrimal implant, and wherein the color identifies the attribute of the lacrimal implant, a luminescent material, and wherein a color reflected by the luminescent material identifies the attribute, a material visible with an ultraviolet light source, and wherein the detection device identifies the attribute when illuminated with the ultraviolet light source, and a material elutable by the lacrimal implant; and wherein the elutable material identifies the attribute.

38. The method according to aspects 36 and 37, optionally including providing a sustained release ocular agent in the lacrimal implant, and wherein the detection device is configured to allow identification of at least one of a type of the ocular agent, a dose of the ocular agent, and an indication of when release of the ocular agent is complete.

39. The method according to aspects 36-38, wherein, the detection device used optionally allows identification of at least one of the lacrimal implant manufacturer, the lacrimal implant manufacturer's lot number, a date the lacrimal implant was implanted, an expiration date of the implant, an indication of a location of where the lacrimal implant was implanted, an indication to identify a physician, and an indication to identify a patient or subject.

40. A method for treating an eye disorder includes inserting a lacrimal implant into at least one lacrimal punctum of a subject, detecting a detection device included in the lacrimal implant, and identifying at least one attribute of the lacrimal implant via the detection device.

41. The method according to aspect 40, wherein the detecting a detection device optionally includes communicating with an RFID chip included in the lacrimal implant, and wherein identifying the attribute includes communicating attribute information between the RFID chip and a separate detector device.

42. The method according to aspects 40 and 41, wherein the detecting a detection device optionally includes detecting a color in the lacrimal implant, and identifying the attribute includes identifying the attribute using the color.

43. The method according to aspects 40-42, wherein the detecting a color in the lacrimal implant optionally includes detecting a color reflected by a luminescent material included in the lacrimal implant.

44. The method according to aspects 40-43, wherein the detecting a color in the lacrimal implant optionally includes detecting a color reflected by a quantum dot included in the lacrimal implant.

45. The method according to aspects 40-45, wherein the detecting a detection device optionally includes detecting a material in the lacrimal implant visible with an ultraviolet light source, and wherein identifying the attribute includes identifying the attribute when the material is illuminated with the ultraviolet light source.

46. The method according to aspects 40-45, wherein the detecting a detection device optionally includes detecting a material elutable by the lacrimal implant, and wherein identifying the attribute of the lacrimal implant includes identifying the attribute from the elutable material.

47. The method according to aspects 40-46, wherein the lacrimal implant used in the method optionally includes a sustained release ocular agent, and wherein the attribute of the lacrimal implant includes at least one of a type of the ocular agent, a dose of the ocular agent, and an indication of when release of the ocular agent is complete.

48. The method according to aspects 40-47, wherein the identifying the attribute optionally includes identifying at least one of the lacrimal implant manufacturer, the lacrimal implant manufacturer's lot number, a date the lacrimal implant was implanted, an expiration date of the implant, an indication of a location of where the lacrimal implant was implanted, an indication to identify a physician, and an indication to identify a patient.

49. An apparatus includes a lacrimal implant insertable at least partially into a lacrimal punctum. The lacrimal implant includes an implant body that includes a detection device. The detection device includes at least one of a ferromagnetic material that is capable of retaining a ferromagnetic property after application and removal of an external magnetic field, an ultrasonically reflective material configured to allow automatic detection of the lacrimal implant with a separate ultrasonic detector device, and a radio frequency identifier (RFID) included in the implant body, wherein the RFID is configured to communicate with a lacrimal implant detector device.

50. The apparatus according to aspect 49, wherein the detection device of embodiment 49 optionally includes the ferromagnetic material, and the ferromagnetic material includes at least one of magnetite, a metallic powder, a metallic ring, and a carbon powder.

51. The apparatus according to aspects 49 and 50, wherein the detection device optionally includes the ultrasonically reflective material. The ultrasonically reflective material is disposed within a biocompatible material of the implant body, and wherein the ultrasonically reflective material is configured to cause the implant body to change shape upon application of ultrasound energy to the lacrimal implant.

52. The apparatus according to aspects 49-51, wherein the ultrasonically reflective material optionally includes a piezoelectric material.

53. The apparatus according to aspects 49-52, wherein an agent for sustained release into an eye is optionally disposed within the implant body.

54. A method of treating an eye disorder includes inserting a lacrimal implant into at least one lacrimal punctum of the subject and detecting the lacrimal implant by detecting a detection device with a separate detector device. The lacrimal implant includes an implant body having the detection device and a supply of an agent disposed in an implant core. The supply in the core provides sustained release of the agent. The detection device includes at least one of a ferromagnetic material that is capable of retaining a ferromagnetic property after application and removal of an external magnetic field, an ultrasonically reflective material configured to allow automatic detection of the lacrimal implant with a separate ultrasonic detector device, and a radio frequency identifier (RFID) included in the implant body that communicates with a lacrimal implant detector device.

55. The method according to aspect 54, wherein the agent optionally includes an agent to treat a glaucoma disease.

56. The method according to aspects 55 and 56, wherein the agent optionally includes an agent to treat at least one of ocular hypertension or primary open angle glaucoma.

57. A detection system includes a light emitting source to provide incident light to a lacrimal implant, an optical filter configured to pass light of a specified wavelength range reflected from a luminescent material of the lacrimal implant, a light detecting device configured to receive the light passed by the filter and to produce a responsive electrical signal when sufficient light is received to indicate proximity of the lacrimal implant, and an indicator, communicatively coupled to the light detecting device, to provide a user indication of plug detection upon receiving the electrical signal.

58. The system according to aspect 57, wherein the light emitting source optionally provides incident light having a first wavelength range and the luminescent material reflects the incident light in a second wavelength range.

59. The system according to aspects 57 and 58, wherein the light emitting source optionally provides incident light in a blue spectrum and the luminescent material reflects the incident light in a green spectrum.

60. The system according to aspects 57-59, wherein the light emitting source optionally provides incident light of a first wavelength range in an infrared spectrum, and the luminescent material reflects the incident light in a different second wavelength range of the infrared spectrum.

61. The system according to aspects 57-60, wherein the indicator optionally provides a visual indication of plug detection.

62. The system according to aspects 57-61, wherein the indicator optionally provides an audible indication of plug detection.

63. A detection system includes a lacrimal implant insertable at least in part into a lacrimal punctum and a lacrimal implant detector device. The lacrimal implant comprising an implant body of biocompatible material. The implant body comprises a ferromagnetic material that is capable of retaining a ferromagnetic property after application and removal of an external magnetic field. The lacrimal implant detector device includes a magnetic field detector circuit, and an indicator device, communicatively coupled to the magnetic field detector circuit, configured to provide an indication upon detection of a magnetic field of the lacrimal implant.

64. The system according to aspect 63, wherein the magnetic field detection circuit optionally includes a Hall Effect sensor.

65. The system according to aspects 63 and 64, wherein the magnetic field detection circuit optionally includes a comparison circuit, communicatively coupled to the magnetic field detection circuit, to provide an electrical signal to the indicator device when a voltage at an output of the Hall Effect sensor exceeds a first threshold value.

66. The system according to aspects 63-65, wherein the comparison circuit optionally provides the electrical signal to the indicator device when a voltage at the output of the Hall Effect sensor exceeds the first threshold value and is also less than a second threshold value.

67. The system according to aspects 63-66, wherein the indicator device optionally provides an audible indication.

68. The system according to aspects 63-67, wherein the indicator device of embodiments 63-67 optionally provides a visual indication.

69. The system according to aspects 63-68, wherein the lacrimal implant detector device optionally includes an elongate housing that includes a proximal end and a distal end, wherein the magnetic field detection circuit includes a magnetic field sensor arranged at or near the proximal end.

70. The system according to aspects 69, wherein the indicator device optionally provides a visual indication and is at a point distal from the magnetic field sensor.

71. The system according to aspects 63-70, wherein the lacrimal implant detection device optionally includes a housing shaped to fit over an eye of a subject.

72. A method includes forming a lacrimal implant of a biocompatible material, providing ferromagnetic material in the lacrimal implant, and exposing the lacrimal implant to a magnetic field such that the lacrimal implant exhibits a ferromagnetic property when no longer exposed to the magnetic field.

73. The method according to aspect 72, wherein the forming a lacrimal implant optionally includes forming an implant body of the biocompatible material, and the providing ferromagnetic material in the lacrimal implant includes disposing the ferromagnetic material within the biocompatible material of the implant body.

74. The method according to aspects 72 and 73, wherein the forming a lacrimal implant optionally includes forming a cavity within a body of the lacrimal implant, providing an implant core within the cavity, wherein the implant core is sized and shaped to provide an agent in an amount sufficient for sustained release to an eye, and the providing ferromagnetic material in the lacrimal implant includes providing ferromagnetic material in the implant core of the lacrimal implant.

75. The method according to aspects 72-74, optionally including forming the implant core with a sheath to house the agent, and the providing ferromagnetic material in the implant core includes disposing the ferromagnetic material in the sheath.

76. The method according to aspects 72-75, wherein the providing ferromagnetic material in the lacrimal implant optionally includes providing magnetite in the lacrimal implant.

77. A method of treating an eye disorder includes inserting a lacrimal implant into at least one lacrimal punctum of the subject and detecting the ferromagnetic property of the lacrimal implant with a lacrimal implant detector device. The lacrimal implant includes an implant body of biocompatible material and a supply of an agent disposed in the implant core. The supply provides sustained release of the agent. The implant body comprises a ferromagnetic material that is capable of retaining a ferromagnetic property after application and removal of an external magnetic field, a cavity within the implant body extending inward into the implant body from an end of the implant body, an implant core within the cavity, wherein the implant core is sized and shaped to provide the agent in an amount sufficient for the sustained release to an eye.

78. The method according to aspect 77, wherein the agent optionally includes an agent to treat a glaucoma disease.

79. The method according to aspects 77 and 78, wherein the agent optionally includes an agent to treat at least one of ocular hypertension or primary open angle glaucoma.

80. A detection system includes a lacrimal implant insertable into a lacrimal punctum, and a lacrimal implant detector device. The lacrimal implant includes an implant body of biocompatible material, and an electrically conductive material within the implant body. The lacrimal implant detector device includes a sensing circuit having a characteristic impedance, a detector circuit configured to detect a change in the characteristic impedance due to proximity of the lacrimal implant to the sensing circuit, and an indicator device, communicatively coupled to the detector circuit, to provide an indication upon detection of the change in the characteristic impedance.

81. The system according to aspect 80, wherein the electrically conductive material of embodiment 80 optionally includes electrically conductive particles disposed within the biocompatible material of the implant body.

82. The system according to aspects 80 and 81, wherein the lacrimal implant of embodiments 80 and 81 optionally includes an implant core comprising a sustained release ocular agent. The implant body includes a cavity extending inward into the implant body from an end of the implant body. The cavity is sized and shaped to receive the implant core, and the electrically conductive material is disposed within the implant core.

83. The system according to aspects 80-82, wherein the implant core optionally includes a sheath to house the agent, and wherein the electrically conductive material is disposed within the sheath.

84. The system according to aspects 80-83, wherein the electrically conductive material optionally includes at least one of steel, silver, gold, and aluminum.
85. The system according to aspects 80-84, wherein the sensing circuit optionally includes a natural response frequency based on the characteristic impedance, and wherein the detector circuit detects the change in the characteristic impedance from a shift in the natural response frequency.
86. The system according to aspects 80-85, wherein the characteristic impedance optionally includes a characteristic inductance, and the detector circuit is configured to detect a change in the characteristic inductance due to proximity of the lacrimal implant to the sensing circuit.
87. The system according to aspects 80-86, wherein the characteristic impedance optionally includes a characteristic capacitance, and the detector circuit is configured to detect a change in the characteristic capacitance due to proximity of the lacrimal implant to the sensing circuit.
88. The system according to aspects 80-87, wherein an agent for sustained release into an eye is optionally disposed within the implant body.
89. A method includes providing a lacrimal implant, detecting the lacrimal implant, without contacting the lacrimal implant, by detecting a change in a characteristic impedance of a sensing circuit due to proximity of the lacrimal implant, and providing information about whether the lacrimal implant is detected to a user or an automated process.
90. The method according to aspect 89, wherein the detecting the change in characteristic impedance optionally includes detecting a shift in a natural response frequency of the sensing circuit.
91. The method according to aspects 89 and 90, wherein the providing the lacrimal implant optionally includes providing the lacrimal implant comprising biocompatible material and an electrically conductive material disposed within the biocompatible material.
92. The method according to aspects 89-91, wherein the providing the lacrimal implant optionally includes providing a lacrimal implant comprising a cavity within a body of the lacrimal implant, wherein the cavity extends inward into the implant body from an end of the implant body, an implant core within the cavity, wherein the implant core is sized and configured to provide sustained release of an agent, and an implant core comprising an electrically conductive material.
93. The method according to aspects 89-92, optionally including providing the implant core with a sheath to house the agent, and providing the electrically conductive material in the sheath.
94. A method of treating an eye disorder includes inserting a lacrimal implant into at least one lacrimal punctum of a subject and detecting the lacrimal implant by detecting a change in a characteristic impedance of a sensing circuit due to proximity of the lacrimal implant to the sensing circuit. The lacrimal implant includes an implant body of biocompatible material, wherein the implant body includes a cavity extending inward into the implant body from an end of the implant body, an implant core sized and configured to provide sustained release of an agent into an eye, wherein the implant core is carried within the cavity of the implant body, a supply of the agent disposed in the implant core, the supply configured to provide the sustained release of the agent, and an electrically conductive material within the implant body.
95. The method according to aspect 94, wherein the agent optionally includes an agent to treat a glaucoma disease.
96. The method according to aspects 94 and 95, wherein the agent optionally includes an agent to treat at least one of ocular hypertension or primary open angle glaucoma.
97. A detection system, includes an image sensor, and an image analyzer circuit. The image analyzer circuit detects a location of an image portion having an image contrast that exceeds the image contrast in other areas of the image by a threshold image contrast value to provide an indication of whether an image of portion of a lacrimal implant is in the image.
98. The system according to aspect 97, wherein the image sensor optionally includes a digital image sensor included in a camera.
99. The system according to aspects 97 and 98, wherein the detection system optionally includes an infrared light emitter, and the image sensor includes an infrared image sensor.
100. A method of treating an eye disorder includes inserting a lacrimal implant into at least one lacrimal punctum of the subject, obtaining an image of the lacrimal punctum region of the subject, and detecting the lacrimal implant by detecting a location of an image portion having an image contrast that exceeds the image contrast in other areas of the image. The lacrimal implant includes an implant body of biocompatible material, wherein the implant body includes a cavity extending inward into the implant body from an end of the implant body, an implant core sized and configured to provide sustained release of an agent into an eye, wherein the implant body cavity is sized and shaped to receive the implant core, and wherein the implant core includes an optical contrast material to optically distinguish the lacrimal implant from a region of an eye, and a supply of the agent disposed in the implant core, wherein the supply to provides the sustained release of the agent.
101. The method according to aspect 100, wherein the agent optionally includes an agent to treat a glaucoma disease.
102. The method according to aspects 100 and 101, wherein the agent optionally includes an agent to treat at least one of ocular hypertension or primary open angle glaucoma.

This section is intended to provide an overview of subject matter of the present patent application. It is not intended to provide an exclusive or exhaustive explanation of the invention. The detailed description is included to provide further information about the present patent application.

DETAILED DESCRIPTION OF THE INVENTION

Figure 1A:
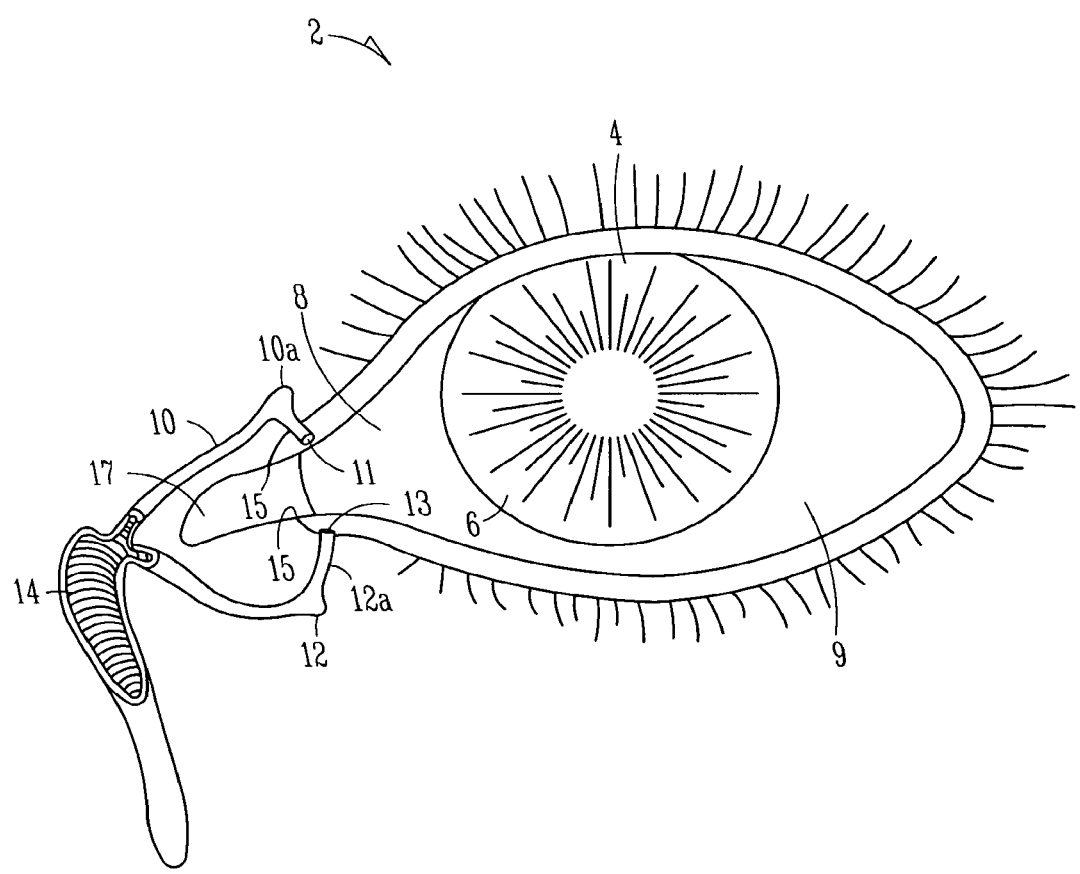
FIGS. 1A and 1B show anatomical tissue structures of the eye suitable for use with various implants, according to embodiments of the present invention.
Figure 1B:
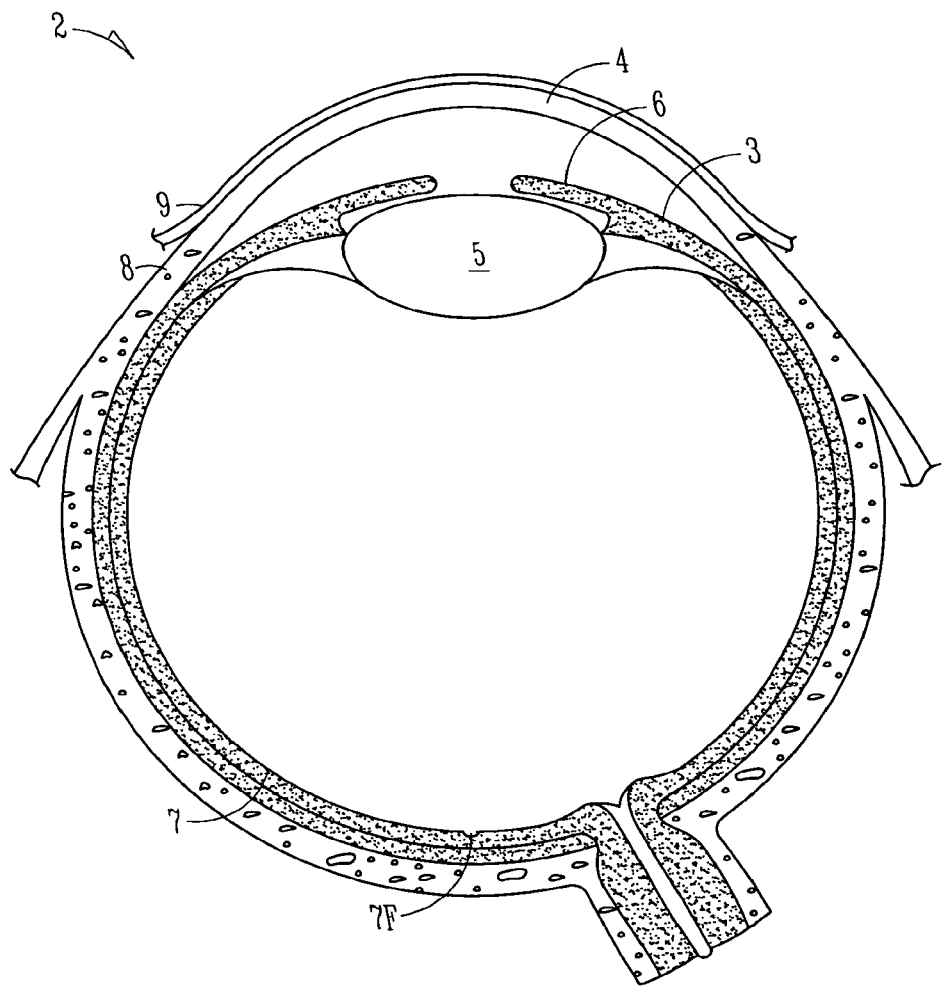

FIGS. 1A and 1B show anatomical tissue structures of an eye 2 suitable for treatment with implants, according to an embodiment of the present invention. Eye 2 includes a cornea 4 and an iris 6. A sclera 8 surrounds cornea 4 and iris 6 and appears white. A conjunctival layer 9 is substantially transparent and disposed over sclera 8. A crystalline lens 5 is located within the eye. A retina 7 is located near the back of eye 2 and is generally sensitive to light. Retina 7 includes a fovea 7F that provides high visual acuity and color vision. Cornea 4 and lens 5 refract light to form an image on fovea 7F and retina 7. The optical power of cornea 4 and lens 5 contribute to the formation of images on fovea 7F and retina 7. The relative locations of cornea 4, lens 5 and fovea 7F are also important to image quality. For example, if the axial length of eye 2 from cornea 4 to retina 7F is large, eye 2 can be myopic. Also, during accommodation, lens 5 moves toward cornea 4 to provide good near vision of objects proximal to the eye.

The anatomical tissue structures shown in FIG. 1A also include the lacrimal system, which includes an upper canaliculus 10 and a lower canaliculus 12, collectively the canaliculae, and the nasolacrimal duct or sac 14. The upper and lower canaliculae terminate in an upper punctum 11 and a lower punctum 13, also referred to as punctal apertures. The punctal apertures are situated on a slight elevation at the medial end of the lid margin at the junction 15 of the ciliary and lacrimal portions near the medial canthus 17. The punctal apertures are round or slightly ovoid openings surrounded by a connective ring of tissue. Each of the punctal openings 11, 13 leads into a vertical portion 10a, 12a of the respective canaliculus before turning horizontally to join its other canaliculus at the entrance of a lacrimal sac 14. The canaliculae are tubular and lined by stratified squamous epithelium surrounded by elastic tissue which permits the canaliculus to be dilated.

In the embodiments described herein, the implant is described as having or including a detection device, or a detectable device. The detection device may be a physical device, a signal transmitting surface or material, a component added to the implant, a detection agent, or it may be a substance or chemical added to the implant during manufacturing giving it certain detectable properties. For example, the detection device may be a detection agent that elutes from the surface of the implant. In another example, the detection device may include a detection signal transmitting surface or material. In some embodiments, the transmitting surface or material may also include a mirrored portion that can reflect light. In some embodiments, the shape of the implant may assist in detection, for example, the implant may change the shape of the cavity and an ultrasound may be used to see the shape change to determine the location of the implant.

It should be understood that a detection device may not be limited to just detection of the presence of the implant, the detection device may also be an identification device capable of detection or identification of characteristics, features or attributes of the implant. Identification of the implant may also include information on the type of implant, or if a therapeutic agent is involved, the type of therapeutic agent, etc. In some embodiments the implant may include a memory device or chip capable of having information written to it that is readable and/or writeable by a detection and/or identification reader. The information may be written either during implant manufacturing or when implanted, optionally using a data writing structure of a tool used to insert the implant. Such information may include: the implant manufacturer, implant manufacturer's lot number, drug or ocular agent type or drug amount or dose in the implant, expiration date, date of implant, indication of when release of the drug is complete, the implanting doctor, an indication of where the implant was implanted, patient's name or other indication to identify the patient, or other information helpful in the detection or identification of the implant. Exemplary systems will facilitate determination of at least the implant lot number, the identification of the active drug or drugs included in the implant, and the total drug quantity or quantities of the implant. The implant may also include a bio-erodable surface that elutes material for identification, or may change color and/or lose color to provide information about the implant. In other embodiments, the transmitting surface or material may also change shape, such as having a pop-up portion, to provide information on the implant, such as when it should be removed or changed.

Figure 2A:
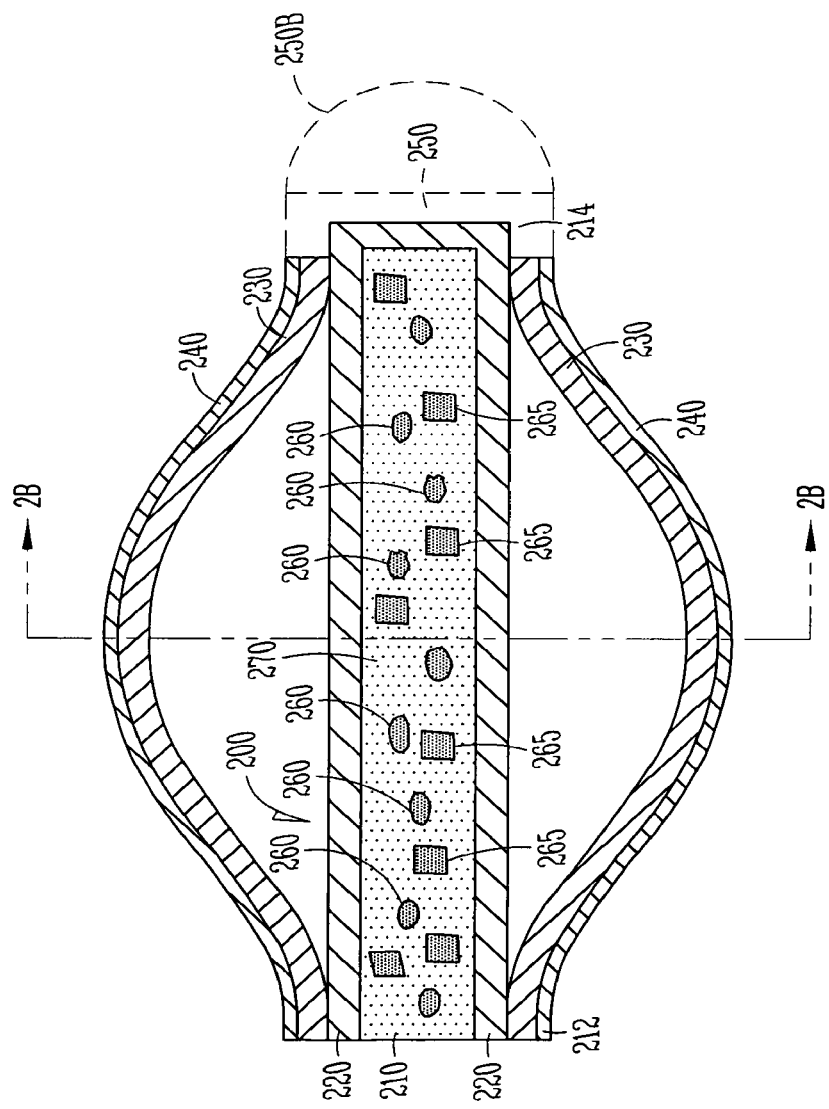
FIG. 2A shows a sectional view of an implant having a core with a detection agent and a therapeutic agent to treat an eye, according to an embodiment of the present invention.

FIG. 2A shows a top cross sectional view of an implant 200 to treat an eye having a detection device, according to embodiments of the present invention. Implant 200 includes a core 210 having a proximal end 212 and a distal end 214 having a detection agent therein. In the embodiment shown, the core 210 also includes one or more therapeutic agents. The core 210 comprises a matrix 270 that contains first inclusions 260 of the detection agent and second inclusions 265 of the therapeutic agent. First and second inclusions 260, 265 may comprise a concentrated form of the agents, for example a liquid or solid form of the agents, and the agents may over time dissolve into matrix 270 of core 210. Matrix 270 can comprise a silicone matrix or the like, and the mixture of the detection agent and therapeutic agent within matrix 270 can be non-homogenous. In many embodiments, the non-homogenous mixture comprises a silicone matrix portion that is saturated with the detection agent and therapeutic agent and an inclusions portion comprising inclusions of the detection agent and therapeutic agent, such that the non-homogenous mixture comprises a multiphase non-homogenous mixture. In some embodiments, matrix 270 encapsulates inclusions 260, 265, and inclusions 260, 265 may comprise microparticles have dimensions from about 1 µm to about 100 µm. The encapsulated inclusions dissolve into the surrounding solid matrix, for example silicone, that encapsulates the micro particles such that matrix 270 is substantially saturated with the detection agent and therapeutic agent, while the detection agent and therapeutic agent are released from the core.

Core 210 fits within a channel of a sheath body 220 on its outer diameter and distal end 214. Sheath body 220 is substantially impermeable to the detection agent and therapeutic agent, so that the detection agent and therapeutic agent are released from an exposed surface on the proximal end 212 of core 210 that is not covered with sheath body 220.

Figure 5:
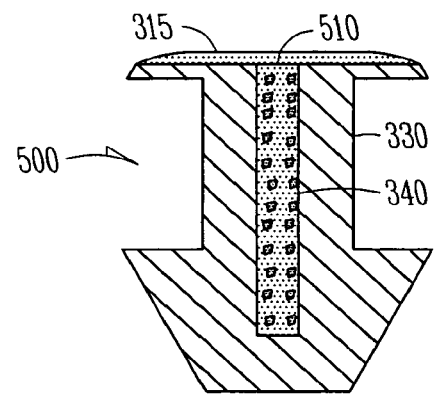
FIG. 5 shows a side cross-sectional view of an implant having a punctum plug and a detection agent within the punctum plug.

Implant 200 may be incorporated with other elements or structures for implantation (see FIG. 5, where the implant is combined with a punctum plug). In the embodiment shown in FIG. 2A, a retention element 230 may be connected to core 210 and sheath body 220 to retain the implant 200 in a hollow tissue structure, for example, a punctum of a canaliculus, as described above.

An occlusive element 240 may be disposed on and around retention element 230. Occlusive element 240 is impermeable to tear flow and occludes the hollow tissue structure and may also serve to protect tissues of the tissue structure from retention element 230 by providing a more benign tissue-engaging surface. Sheath body 220 includes a sheath body portion 250 that connects to retention element 230 to retain sheath body 220 and core 210. Sheath body portion 250 can include a stop to limit movement of sheath body 220 and core 210. The sheath body portion 250 may also have a shape 250B for easier insertion.

Figure 2B:
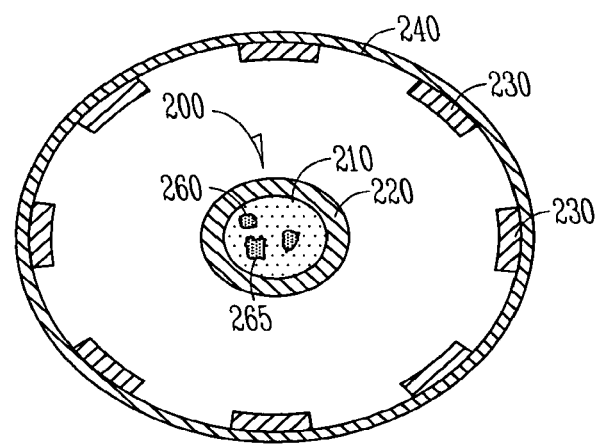
FIG. 2B shows a side cross-sectional view of the implant of FIG. 2A.

FIG. 2B shows a side cross sectional view of the implant 200 of FIG. 2A. Implant 200 is cylindrical and shown with a circular cross-section with the core 210 in the center. Sheath body 220 comprises an annular portion disposed on core 210. In the embodiment shown, retention element 230 comprises several longitudinal struts that are connected together near the ends of the retention element. Although longitudinal struts are shown, circumferential struts can also be used. Occlusive element 240 is supported by and disposed over longitudinal struts of retention element 230 and may comprise a radially expandable membrane or the like. The struts may also be used as a detection device for the implant.

The retention element 230 comprises an appropriate material that is sized and shaped so that the implant can be easily positioned in the desired tissue location, for example the punctum or canaliculus. The retention element is mechanically deployable and typically expands to a desired cross sectional shape, for example with the retention element comprising a super-elastic shape memory alloy such as Nitinol™. Other materials in addition to Nitinol™ can be used, for example resilient metals or polymers, plastically deformable metals or polymers, shape memory polymers and the like for example spring stainless steel, Eligloy®, tantalum, titanium, cobalt chromium to provide the desired expansion. The retention element may be bio-degradable or non-biodegradable depending on the desired treatment time and whether the patient requires physician follow up. This expansion capability permits the implant to fit in hollow tissue structures of varying sizes, for example canaliculae ranging from 0.3 mm to 1.2 mm (i.e. one size fits all). Although a single retention element can be made to fit canaliculae from 0.3 to 1.2 mm across, a plurality of alternatively selectable retention elements can be used to fit this range if desired, for example, a first retention element for canaliculae from 0.3 to 0.9 mm and a second retention element for canaliculae from 0.9 to 1.2 mm. The retention element has a length appropriate to the anatomical structure to which the retention element attaches, for example, a length of about 3 mm or less for a retention element positioned near the punctum of the canaliculus.

Although the sheath body 220 and core 210 are attached to one end of the retention element 230 as described above, in many embodiments the other end of retention element is not attached to core and sheath body so that the retention element can slide over the sheath body and core while the retention element expands. This sliding capability on one end is desirable as the retention element will typically shrink in length as the retention element expands in width to assume the desired cross sectional width. In addition, the core of the device may be replaceable with the sheath body remaining in place. Alternatively, the sheath body may be replaceable within the retention element to provide for exchange of the core to replenish the supply of therapeutic agent to the device.

The occlusive element 240 comprises an appropriate material that is sized and shaped so that the implant can at least partially inhibit, even block, the flow of fluid through the hollow tissue structure, for example lacrimal fluid through the canaliculus. The occlusive material shown is a thin walled membrane of a biocompatible material, for example silicone, that can expand and contract with the retention element. The occlusive element is formed as a separate thin tube of material that is slid over the end of the retention element and anchored to one end of the retention element as described above. Alternatively, the occlusive element can be formed by dip coating the retention element in a biocompatible polymer, for example silicone polymer. The thickness of the occlusive element can be in a range from about 0.03 mm to about 0.15 mm, and often from about 0.05 mm to 0.1 mm.

While the above embodiment was described using a therapeutic agent with the detection agent, it is envisioned that implant 200 may be used without the therapeutic agent, or that two or more detection agents may be used in combination.

The implant core disclosed above comprises detection and therapeutic agents and materials to provide sustained release of the detection and therapeutic agents. The detection and therapeutic agents migrate from the core to the target tissue, for example tissues of the eye. In some embodiments, the therapeutic agent may comprise a hydrophobic compound capable of penetrating the tissues of the eye, for example latanoprost, and the detection agent may comprise a water soluble compound, for example fluorescein, that is capable of elution from the core to the front surface of the eye for detection with limited penetration of the ocular tissues. The detection and therapeutic agents may optionally be only slightly soluble in the matrix so that the release rate remains "zero order" for the lifetime of the release of the detection and therapeutic agents when dissolved in the matrix and available for release from the exposed surfaces of the core. As the detection and therapeutic agents diffuse from the exposed surfaces of the core to the tear or tear film, the rate of migration from the core to the tear or tear film is related to the concentration of detection and therapeutic agents dissolved in the matrixes. In some embodiments, the concentration of detection and therapeutic agents dissolved in the core may be controlled to provide the desired rate of release of the detection and therapeutic agents. In some embodiments the desired rate of release of the detection agent may be the same as the desired rate of release of the therapeutic agent. In some embodiments the desired rate of release of the detection agent may be different than the desired rate of release of the therapeutic agent. The detection and therapeutic agents included in the core can include liquid, solid, solid gel, solid crystalline, solid amorphous, solid particulate, and/or dissolved forms of the detection and therapeutic agents. In some embodiments, the core comprises a silicone matrix containing the detection and therapeutic agents.

The core can be made from any biocompatible material capable of providing a sustained release of the detection and therapeutic agents. Although the core is described above with respect to embodiments comprising a matrix with a substantially non-biodegradable silicone matrix with particles of the agents located therein that dissolve, the core can include any structure that provides sustained release of the detection and therapeutic agents, for example biodegradable matrix, a porous core, liquid core and solid core. The structures can be adapted to release the detection agent and therapeutic agent in therapeutic amounts over a period of time from about one to twelve months after the structure is inserted into the eye. In some embodiments the release rate for the detection and therapeutic agents may be the same or similar. In other embodiments the release rate for the detection and therapeutic agents may be different, with the therapeutic agent being released at a higher or lower rate than the detection agent. In some embodiments, the detection agent is only released when the therapeutic agent is finished.

In some embodiments, the detection agent and therapeutic agent may have separate cores, wherein, a first core may release the therapeutic agent until it is gone and then a second core releases the detection agent to let the patient know that the implant needs to be replaced. In specific embodiments, the second core may comprise a bio-erodable material over a dye, such that the erodable material erodes so as to uncover and release the dye when the first core needs to be replaced. The released dye can be visible to the patient at a desired interval post implantation. In a specific embodiment, the patient may wake up with a blue eye and know that the core needs to be replaced and contact his or her treating physician, for example about three months after the implant was placed as determined by the intended erosion time of the erodable material over the dye.

Figure 3A:
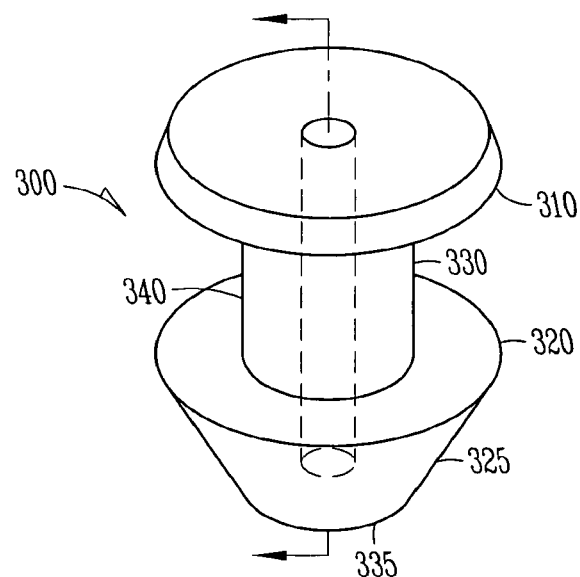
FIG. 3A schematically illustrates an implant in the shape of a punctum plug for use in the eye.
Figure 3B:
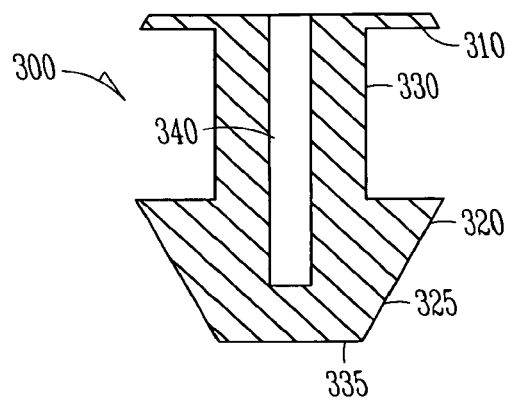
FIG. 3B shows a side cross-sectional view of the implant of FIG. 3A.

FIGS. 3A and 3B schematically illustrate one embodiment of a lacrimal insert in the shape of a punctum plug 300 for use with an implant that includes a detection device associated with the punctum plug 300. The detection device includes any device used to identify an attribute of the plug 300. In some embodiments, the attribute may include physical characteristics of the plug, such as size, shape, or composition of the plug. In other embodiments, the attribute may include information related to the plug, such the type or style, when it was implanted, track the serial number, or other information relevant to the plug.

Some embodiments of the punctum plugs use different colors to distinguish the plugs. The punctum plug may be formed with a color material, or the color may be added, such as a color coating applied to the punctum plug. In another embodiment, a colored core may be inserted into a channel of the plug, the colored core having a different color than the punctum plug, or the colored core have different colors identifying a physical characteristic, feature or attribute of the punctum plug 300. The different colors of the punctum plug and/or core may also be used to identify different therapeutic agents associated with the punctum plug, when the punctum plug is used for drug delivery implant, discussed below. The colors may also identify different compounds, dosage or release rates of the therapeutic agents. In specific embodiments, a red plug corresponds to a glaucoma treatment, a green plug corresponds to an antibiotic treatment, and a blue plug corresponds to an allergy treatment. Although many dyes can be used to provide the desired colors, some embodiments may employ spectral encoding with quantum dots, such that a single excitation wavelength can be used to stimulate many emission wavelengths, for example blue light used to stimulate red, orange, yellow and green emissions. In some embodiments, the detection device is an elutable material. The attribute of the punctum plug is identified when the material is eluted into the eye.

In some embodiments, the detection device may include metal pieces attached to the punctum plug, such as bands or rings, or a metallic or carbon powder within the punctum plug. Also, the detection device may be inserted into a channel of the punctum plug or formed within the punctum plug.

The punctum plug 300 includes a collarette 310 at a proximal end which rests on the exterior of the punctum 11, 13 (see FIG. 1A), a bulb 320 with a tapered portion 325 terminating in a tip 335 at a distal end that blockingly projects into the canaliculus 10, 12 (see FIG. 1A), and a body portion 330 connecting the collarette 310 and the bulb 320. The punctum plug 300 is approximately 2.0 mm in length. The bulb 320 is designed to prevent the punctum plug 300 from being easily dislodged from the canaliculus 10, 12, and may be tapered for ease of insertion into the punctum 11, 13. The collarette 310 is designed to have a diameter to prevent the punctum plug 300 from completely entering the canaliculus 10, 12, and is preferably smooth to minimize irritation of the eye 2. The plug body portion 330 of the punctum plug 300 is essentially a non-functional connection between the collarette 310 and the bulb 320 portions. The collarette 310 includes a cavity 340 or channel extending into the body portion 330 into which a detection device is placed. The size and shape of the cavity 340 is selected to hold the device in place. In other embodiments, thedevice is sized to fit into a typical cavity opening in a punctum plug. In some embodiments, the detection device is molded into the body. Example detection devices include a radio frequency identifier (RFID) device, magnetic or ferromagnetic device, ultrasonic device, ultraviolet device, infrared device, a detection agent, a luminescent material, an electrically conductive material, and an identification agent. In some embodiments, the detection device is visible. In some embodiments, the detection device may be detected with a separate detector device.

Figure 7A:
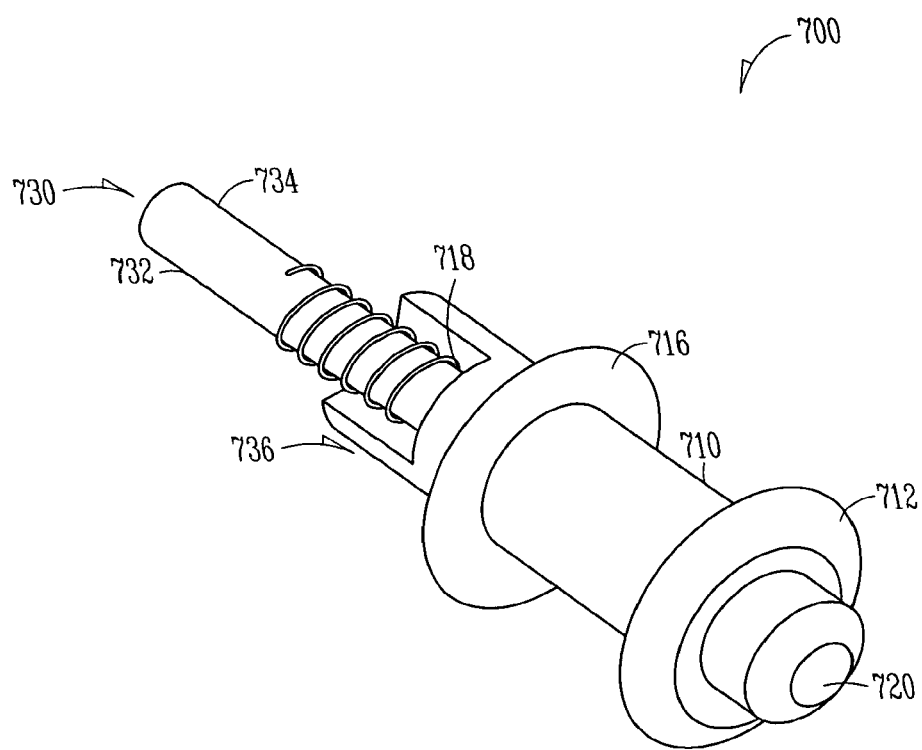
FIGS. 7A and 7B show an implant comprising a silicone body, a core and retention structures, according to embodiments of the present invention.
Figure 7B:
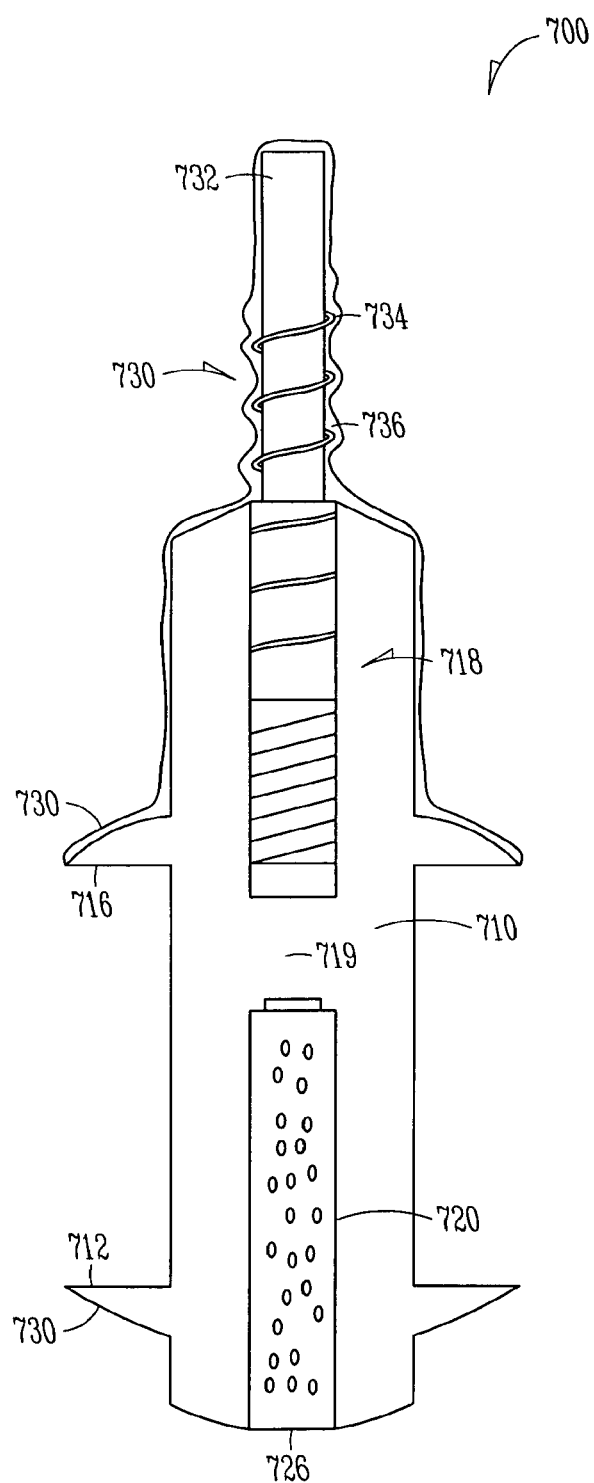

In some embodiments, the tip 335 of the punctum plug 300 is closed, in other embodiments, an opening 350 in the tip 335 at the distal end allows access to the cavity 340, allowing fluid flow through the punctum plug 300 (for example, see FIG. 7B). The body 310 may be molded or otherwise formed from a flexible material, such as silicone, that is biocompatible. The material selected may also be permeable or impermeable to detection agents placed within the cavity 340.

In some embodiments, an optional head structure 315 (see FIG. 5) is provided over the collarette 310 to enclose the cavity 340. In some embodiments, the head structure 315 is made of the same material as the body. In some embodiments, the head structure is made of a biocompatible material, preferably soft and flexible material, which is permeable to any detection agents that might be placed in the cavity 340. In some embodiments, when the punctum plug 300 is in place, detection agents may be deployed from the cavity 340 through the head structure into the tears of the lacrimal lake where the agents mix with the tears and allow detection of the agents.

Figure 4:
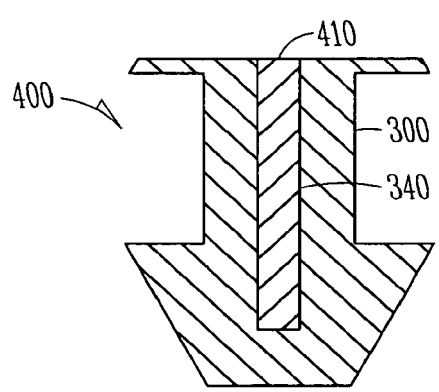
FIG. 4 shows a side cross-sectional view of an implant having a punctum plug and a detection device within the punctum plug.

FIG. 4 schematically illustrates one embodiment of a lacrimal implant 400 having a punctum plug 300. The punctum plug 300 is insertable at least partially into a lacrimal punctum. The punctum plug includes a plug body having cavity 340 sized and shaped to receive a plug core. In some embodiments, the plug core includes a detection device 410. In some embodiments, the plug core includes both a detection device 410 and a sustained release therapeutic agent. In the embodiment shown, a detection device 410 is positioned within the cavity 340 of the punctum plug 300. The device 410 may be any device that aids in the automatic detection and/or identification of the implant 400 by a separate detector device when positioned in the punctal aperture. In some embodiments, the detection device 410 may be a detection signal transmitting surface or material, with the signal from the transmitting surface or material allowing detection of the implantable body when the transmitting surface or material is obscured within the punctum. In some embodiments, the detection device 410 identifies an attribute of the implant from among a plurality of alternative attributes of implants. In one embodiment, the transmitting surface or material comprises a radio signal transmitting surface of an RFID chip capable of detection with a RFID detector, the signal comprising a radio signal identification signal. In other embodiments, the signal transmitting surface or material includes a magnetic signal transmitting surface or material capable of detection with a magnetic detector or an echographic surface of an ultrasonically reflective material capable of detection with an ultrasonic detector.

RFIDs may be made in very small sizes. For example, Hitachi has developed the "μ-chip" that is 0.4 mm×0.4 mm, and they are currently in development of a RFID chip as small as 0.05 mm×0.05 mm. In the embodiment shown in FIG. 4, the RFID may be inserted into the channel of the punctum plug. The size and shape of the channel should be sized hold the selected RFID chip in place, for example, by adhesives or frictional fit. In another embodiment, the RFID may be incorporated into the punctum plug during plug manufacturing, for example, the RFID chip may be molded into the plug (see e.g., FIG. 7A). To determine the presence of a RFID punctal plug, a RFID detection system may be used that can transmit an audible signal or a light can flash to signify the RFID punctum, for example, if the RFID punctum is in place. In other embodiments, the RFID device may also transmit other characteristics of the implant. If the patient is using the detection system, he/she can transmit the signal via a cell phone or internet connection to the clinician.

Ferromagnetic materials may also be used as detection device 410 in the lacrimal implant. Ferromagnetic materials include any material capable of detection with a magnetic detection system. In some embodiments, the ferromagnetic material retains a ferromagnetic property (e.g., a magnetic field) detectable with the detector device. The detector device may generate a light flash or sound when the property is detected. Examples, of ferromagnetic materials include magnetite, a metallic powder, a metallic ring, and a carbon powder.

Ultrasonic materials may also be used as detection device 410 in the lacrimal implant. Ultrasonic materials include any ultrasonically reflective material capable of detection with an ultrasonic detection system. The ultrasonic material may be a piezoelectric material embedded in the plug that when coupled to the detector device (e.g., placed on the plug using a coupling medium) would transmit a signal to the user (visual or audible). In some embodiments, ultrasonic material may reflect incident ultrasonic energy for detection by the detector device. In some embodiments, the ultrasonically reflective material causes the plug body to change shape upon application of ultrasound energy to the lacrimal implant.

Luminescent materials may be used as the detection device 410. A luminescent (e.g., a quantum dot) of the punctum plug 300 is stimulated with a light source. The luminescent absorbs a higher power/lower wavelength form of light and converts the incident light into a lower power/higher wavelength form of light which is emitted or reflected. The lacrimal implant 300 is detected when the expected higher wavelength form of light is detected by the detector device.

Electrically conductive materials may be used as the detection device 410. In some embodiments, the detector device includes a sensing circuit. To detect the lacrimal implant 300, the detector is positioned near the punctum. The electrically conductive material of the detection device 410 causes a change in a characteristic impedance of the sensing circuit due to proximity of the punctum plug to the sensing circuit.

FIG. 5 schematically illustrates one embodiment of a lacrimal implant having a punctum plug 500 and detection device 510, such as a core with a detection agent. In the embodiment shown, the detection device 510 is positioned within the channel 340 of the punctum plug 500. The detection device 510 may be any device or materials that aids in the detection and/or identification of the implant 500 when positioned in the punctal aperture. Examples of suitable detection devices include detection signal transmitting surfaces or materials, such as materials visible with an ultraviolet light (UV) source, materials visible with an infrared light source, materials visible with a visible light source, or other materials visible with other light sources. In one embodiment, the detection signal transmitting surface or material elutes fluorescein from the implant or co-elutes with a therapeutic agent. In another embodiment, the detection signal transmitting surface or material includes microdots or quantum dots that can be visualized using an infrared or UV light source.

The embodiment of the lacrimal implant 500 shown in FIG. 5 further includes the optional head 315 that is permeable to the detection agents. In one embodiment, the detection device is core 510, having a detection agent and a therapeutic agent. When the implant 500 is in place, the agents are deployed from the proximal end 212 of the core 510 through the permeable head 315 into the tears of the lacrimal lake where the agents mix, as eye drops do, with the tears and move to the eye, where they can be detected.

The detection agent and/or therapeutic agent disclosed may also be combined with the delivery of therapeutic agents, such as disclosed in U.S. application Ser. No. 11/695, 537, titled "Drug Delivery Methods, Structures, and Compositions for Nasolacrimal Systems"; U.S. application Ser. No. 11/695,545, titled "Nasolacrimal Drainage System Implants for Drug Therapy"; U.S. App. No. 60/871,867, titled "Drug Delivery Implants for Inhibition of Optical Defects"; U.S. App. No. 60/970,709, titled "Nasolacrimal Drainage System with Implants for Drug Delivery"; and U.S. App. No. 60/970,820, titled "Multiple Drug Delivery Systems and Combinations of Drugs with Punctal Implants", the full disclosures of which are incorporated herein by reference in their entirety.

Figure 6:
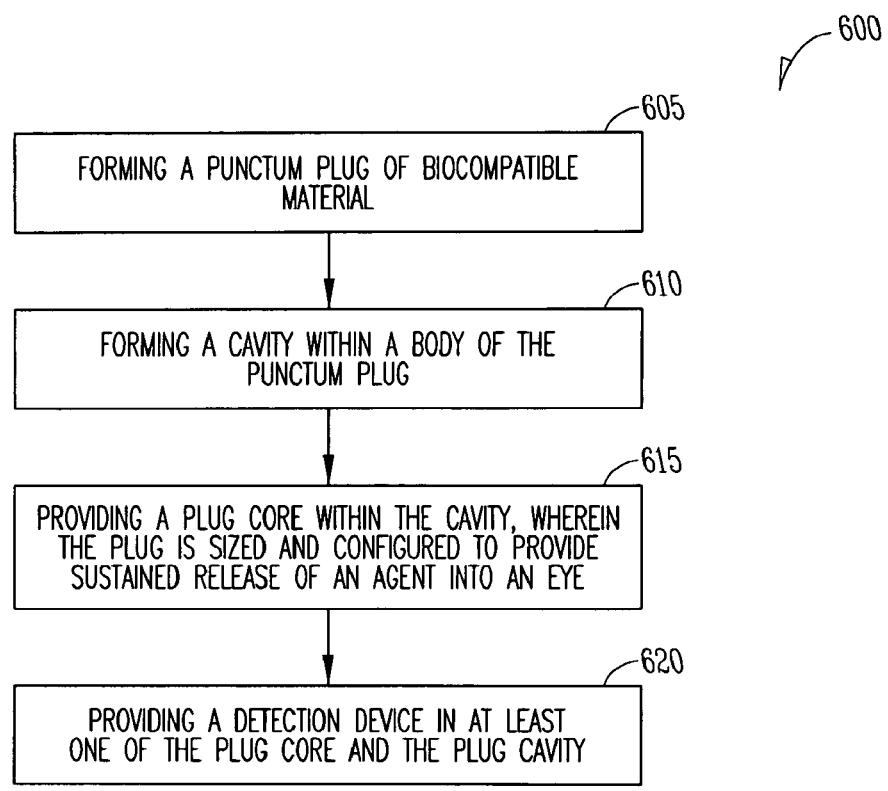
FIG. 6 is a flow diagram of an embodiment of a method of making a device-detectable lacrimal implant.

FIG. 6 is a flow diagram of an embodiment of a method 600 of making a device-detectable lacrimal implant. At block 605, a lacrimal implant in the shape of a punctum plug is formed of biocompatible material. At block 610 a cavity is formed within a body of the punctum plug. At block 615, a plug core is provided within the cavity. In some embodiments, the plug core is sized and configured to provide sustained release of an agent into an eye of a patient or subject. At block 620, a detection device is provided in at least one of the plug cavity and the plug core. The detection device allows automatic detection of the punctum plug with a separate detector device.

A device-detectable lacrimal implant can be used in a method to treat an eye disorder. A lacrimal implant such as a punctum plug is inserted into at least one lacrimal punctum of the subject. The punctum plug body includes a cavity extending inward into the plug body from an end of the plug body. A plug core is carried within the plug body. The plug core includes a supply of an agent and the core provides sustained release of the agent into the eye. The detection device allows automatic detection of the lacrimal implant with a separate detector device. Detecting the detection device with the separate detector device provides detection of the lacrimal implant. In some embodiments, the agent treats a glaucoma disease. The glaucoma disease may be at least one of ocular hypertension or primary open angle glaucoma.

Referring now to FIGS. 7A and 7B, a lacrimal implant, for example a punctum plug 700, is shown which comprises a silicone body 710, a detection device 720 and a retention structures 730, according to embodiments of the present invention. Body 710 comprises a proximal channel 714 sized to receive detection device 720. Body 710 comprises a distal channel 718. Distal channel 718 can be sized to receive a hydrogel rod 732. A partition 719 may separate the proximal channel from the distal channel. A filament 734 can be embedded in body 710 and wrapped around hydrogel, rod 732 to affix hydrogel rod 732 to body 710. In some embodiments, an RFID "µ-chip" or integrated circuit can be positioned within silicone body 710, for example molded within partition 719. In some embodiments, a "µ-chip" can be placed in one of the channels during manufacture of the implant prior to insertion of the drug core or hydrogel rod, as appropriate.

In one embodiment, the detection device 720 includes a core, for example core 210 discussed above. The core insert and manufacture of the core insert are described in U.S. application Ser. Nos. 11/695,537 and 11/695,545, the full disclosures of which are incorporated herein by reference. Although a core insert is shown, some embodiments may comprises a drug reservoir, a semi-permeable membrane, a drug coating or the like, as described in U.S. Pat. No. 6,196,993 in the name of Cohan and U.S. application Ser. No. 10,899,416 in the name of Prescott; Ser. No. 10/899,417 in the name of Prescott; Ser. No. 10/762,421 in the name of Ashton; Ser. No. 10/762,439 in the name of Ashton; Ser. No. 11/571,147 in the name of Lazar and Ser. No. 10/825,047 in the name of Odrich, the full disclosures of which are herein incorporated by reference for all purposes.

Retention structures 730 may comprise hydrogel rod 732, hydrogel coating 736, protrusions 712 and protrusion 716. Hydrogel rod 732 can be inserted through the punctum into a canalicular lumen in a narrow profile configuration. After insertion into the lumen hydrogel rod 732 and hydrogel coating 736 can hydrate expand to a wide profile configuration. Protrusions 712 and protrusion 716 can retain implant 700 in the lumen, for example while the hydrogel coating and rod expand.

Figure 8A:
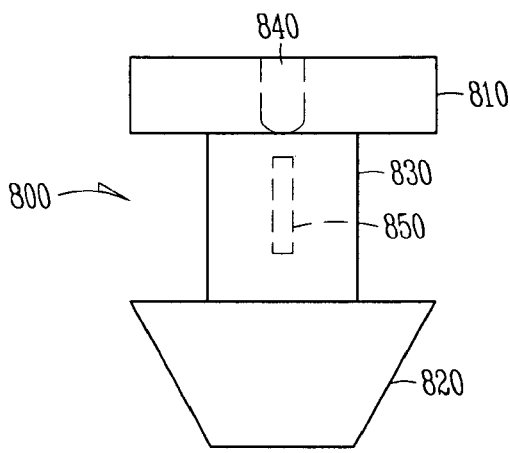
FIGS. 8A and 8B show different embodiments of an implant to treat an eye that encompasses punctum plugs with a detection device within.
Figure 8B:
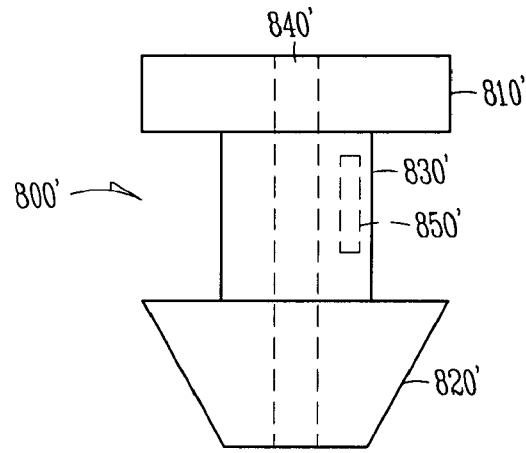

FIGS. 8A and 8B show lacrimal implants 800 and 800' that encompass punctum plugs incorporating detection devices, according to an embodiment of the present invention. In the treatment of ophthalmic ailments where it is desired to prevent or decrease the drainage of lacrimal fluid and/or medication from the eye, the punctal aperture in one or both of the upper and lower lids are to be blocked by implants, two respective embodiments of which are shown in FIGS. 8A and 8B. Referring initially to the embodiment of FIG. 8A, the implant 800 has a blunted tip or barb portion 820 at a distal end, a middle neck or waist portion 830 of somewhat smaller diameter than the tip, and a smooth disc-like head portion 810 at a proximal end of relatively larger diameter. The head portion 810 is provided with a central bore opening 840 adapted to receive the projecting tip of an inserter tool to provide a releasable grip on the therapeutic implant as it is manipulated for insertion, as hereinafter described. Within the plug body is a detection device 850, which may be any of the detection devices described above. The detection device 850 allows detection of the punctum plug and identifies an attribute of the punctum plug.

FIG. 8B shows a hollow lacrimal implant 800' that is of generally similar dimensions to the first-described embodiment having a blunted tip or barb portion 820', a middle neck or waist portion 830' of somewhat smaller diameter than the tip, a smooth disc-like head portion 810' of relatively larger diameter, a central bore 840' extending through the plug and a detection device 850', which may be any of the detection devices described above. The central bore 840' allows fluid flow from a proximal end to distal end of the implant 800'.

In some embodiments of the invention, the detection devices as described herein are incorporated in a punctum plug as described in U.S. App. Pub. No. 2005/0197614, the full disclosure of which is incorporated herein by reference. A gel can be used to form the therapeutic implant 800, 800' and the gel can swell from a first diameter to a second diameter in which the second diameter is about 50% greater than the first diameter. Along with incorporating the detection devices, the gel can also be used to entrap therapeutic agents, for example within a microporous structure in which the agents are uniformly dispersed, and the gel can slowly elute the therapeutic agents into the patient. Various therapeutic agents are described in U.S. Provisional Application No. 60/550,132, entitled "Punctum Plugs, Materials, And Devices", the full disclosure of which is incorporated herein by reference, and may be combined with the gels and devices described herein.

Figure 9:
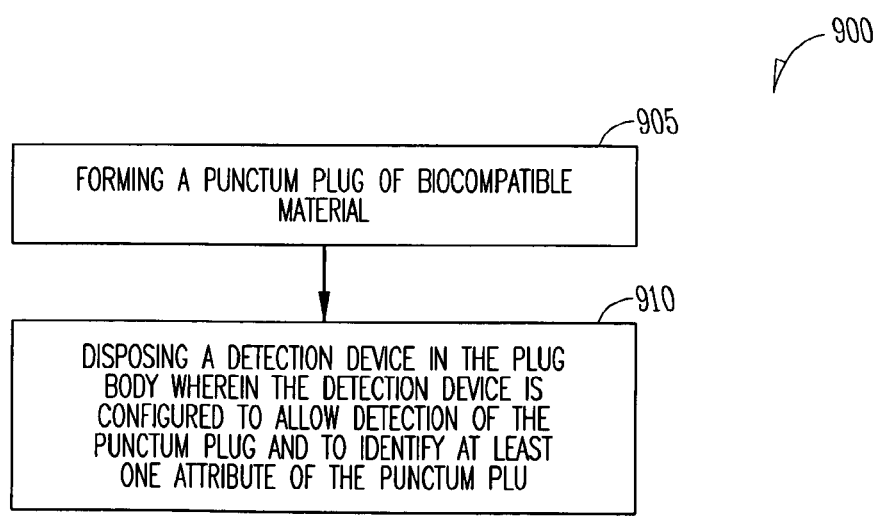
FIG. 9 is a flow diagram of another embodiment of a method of making a device-detectable lacrimal implant.

FIG. 9 shows a flow diagram of another embodiment of a method 900 of making a device-detectable lacrimal implant. At block 905, a lacrimal implant in the shape of a punctum plug having a plug body is formed of biocompatible material. At block 910, a detection device is disposed in the plug body. The detection device allows detection of the punctum plug and identifies one or more attributes of the punctum plug. The detection device may be any of the detection described herein.

A device-detectable lacrimal implant can be used in a method of treating an eye disorder. In such a method, a punctum plug is inserted into at least one lacrimal punctum of a subject. A detection device included in the punctum plug is detected, and the device is used to identify at least one attribute of the punctum plug via the detection device.

Figure 10:
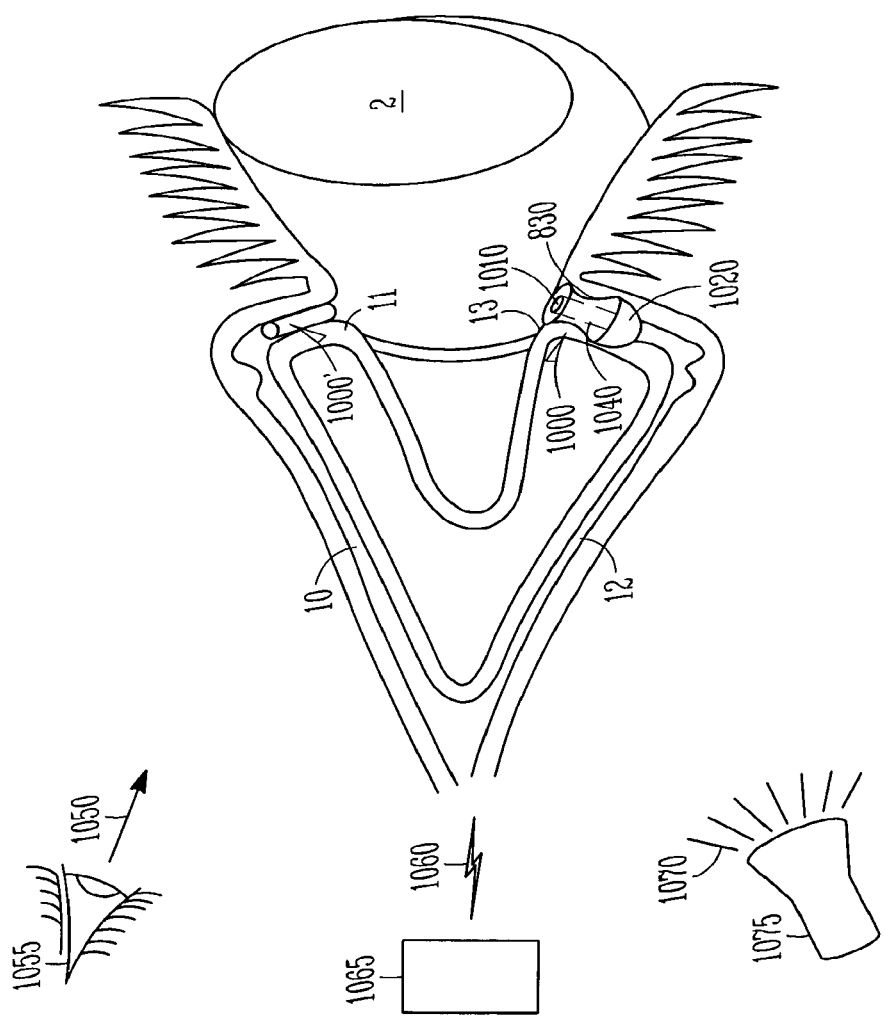
FIG. 10 shows implants containing detection devices as applied to the eye.

FIG. 10 shows lacrimal implants having detection devices as applied to the eye. In the embodiment shown, an implant 1000 is designed for insertion into the lower punctal aperture 13 of the eye 2, and along the canaliculus 12 communicating with the aperture. The implant 1000 includes a punctum plug having a collarette 1010 at a proximal end, a flared portion 1020 at a distal end, a neck portion 1030 and a detection device 1040. The collarette 1010 is designed for seating against the aperture 13. The detection device 1040 may determine if the implant is in the desired position, and/or if the implant continues to elute therapeutic agents, as discussed above. Many different detection devices are contemplated, such as RFID chip, magnetic materials, ultrasonic materials, microdots, eluting detection agents, such as fluorescein, and others know in the art. The implant 1000 may be used to block fluid flow, or may have a hollow portion allowing fluid flow (for example, see FIG. 8B), depending on the requirements.

FIG. 10 further shows a lacrimal implant 1000' containing a detection device may also have a therapeutic agent, such as implant 200 disclosed herein, that is a substantially cylindrical in shape that has been inserted into the upper punctum aperture 11, to block the flow of tears to canaliculus 10. Implant 1000' may also be an occlusive plug of some inert biocompatible material having the detection device within, such as implant 800 disclosed herein.

The implant 1000 and therapeutic implant 1000' can be used in any desired combination, either separately or in combination (shown in FIG. 10). For example, implant 1000' can be positioned in the lower canaliculus and implant 1000 can be positioned in the upper canaliculus. Alternatively, two of the same implants 1000 or 1000' can be positioned in both canaliculae.

The detection devices can be detected many different ways. For example, in some embodiments, the devices may be detected or viewed 1050 by an eye 1055. In other embodiments, the devices may communicate 1060 with different detection systems 1065, depending on the implanted device. For example, the detection system 1065 may include a RFID detection system to detect a RFID chip, a magnetic detector system to detect a magnetic material, an ultrasonic detector system to detect ultrasonically reflective material. In still other embodiments, the detection devices may include materials that may be detected 1070 with alternate light sources 1075, such as an ultraviolet light source or an infrared light source.

The lacrimal implants containing a detection device can be used in a method to treat an eye disorder. In such a method, a lacrimal implant, such as a punctum plug is inserted into at least one lacrimal punctum of the subject. The body of the punctum plug includes any of the detection devices described herein. A supply of an ocular agent is disposed in the core of the punctum plug. The supply provides the sustained release of the agent. The lacrimal implant is detected by detecting the detection device with a separate detector device. In some embodiments, the agent is configured to treat a glaucoma disease. For example, the glaucoma disease may include at least one of ocular hypertension or primary open angle glaucoma.

To detect a magnetic material, in some examples the detection device includes a ferromagnetic material disposed within the body of the lacrimal implant. The ferromagnetic material retains ferromagnetic properties after removal of an externally applied magnetic field. In certain embodiments, the ferromagnetic material includes magnetite ($Fe_3O_4$).

In some embodiments, the ferromagnetic material is disposed within the biocompatible material of the implant body. Magnetic domains are a common physical trait of ferromagnetic material. By inducing the magnetic domains of the ferromagnetic material to align when molded within the biocompatible material of the implant, the magnetic field of the plug approaches that of the inducing magnetic field. The lacrimal implant may then be detected with a magnetic field sensor.

Figure 11A:
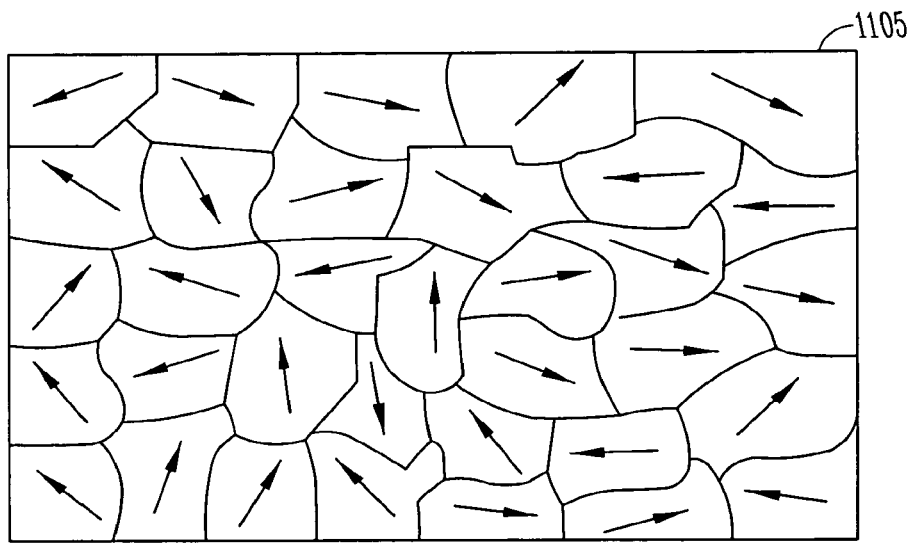
FIGS. 11A, 11B are illustrations to explain inducing the magnetic domains to align in ferromagnetic particles.
Figure 11B:
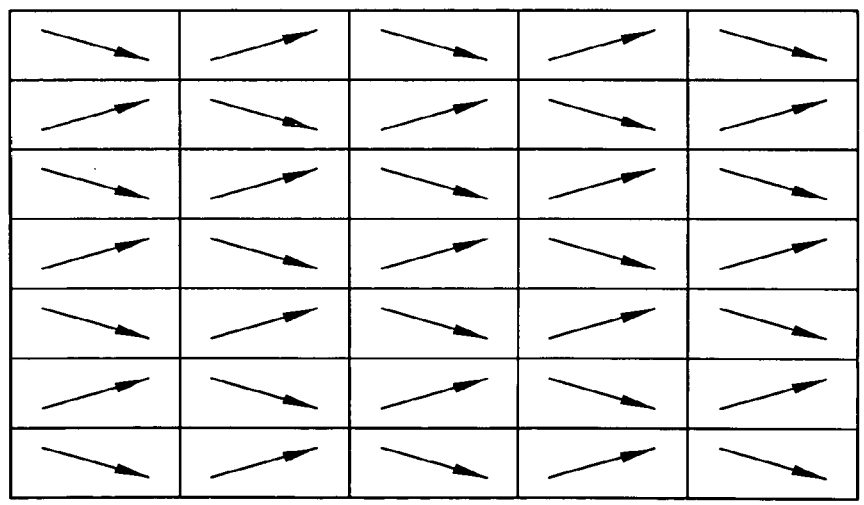

FIGS. 11A, 11B are illustrations to explain inducing the magnetic domains to align in ferromagnetic particles. The illustrations can be found in Ulaby, Fawwaz T., Electromagnetics for Engineers, 146 (2004). FIG. 11A represents the ferromagnetic particles 1105 prior to magnetization. The magnetic domains are randomized. FIG. 11B represents the aligned magnetic domains of the particles after magnetization through exposure to an external magnetic field. This alignment is due to coupling forces between dipole moments of each constituent magnetic domain.

Figure 12:
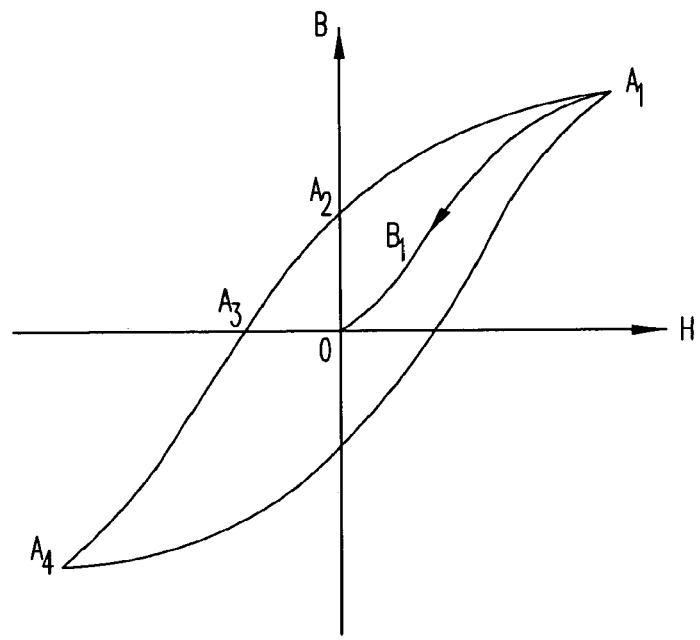
FIG. 12 is a B-H curve used to describe the behavior of ferromagnetic materials when exposed to magnetization.

The behavior of ferromagnetic materials when exposed to magnetization can also be described using the B-H curve of FIG. 12. The amplitude of the externally applied field H determines the total magnetic flux density B within the material. The un-magnetized state is indicated at the origin as O. The curve shows that the inducing field causes magnetization of domains to a maximum saturation, $H_{max}$ and $B_{max}$ at point $A_1$. When the externally applied field H returns to zero, the value of the flux density of the particles does not return to zero, but is offset by some hysteresis error $B_r$ at point $A_2$. This offset is sometimes referred to as residual flux density. The ferromagnetic material, and thus the punctum plug, is now similar to a permanent magnet due to a large number of domains remaining aligned.

If the lacrimal implant 1000 of FIG. 10 is a punctum plug and includes a drug in the punctum plug body, ferromagnetic particles and the drug may be disposed within the plug body. As described above, the implant may include a sheath on the outer surface of the implant. The porosity of the sheath allows the drug to leach out from the plug but retains the ferromagnetic particles.

Figure 13:
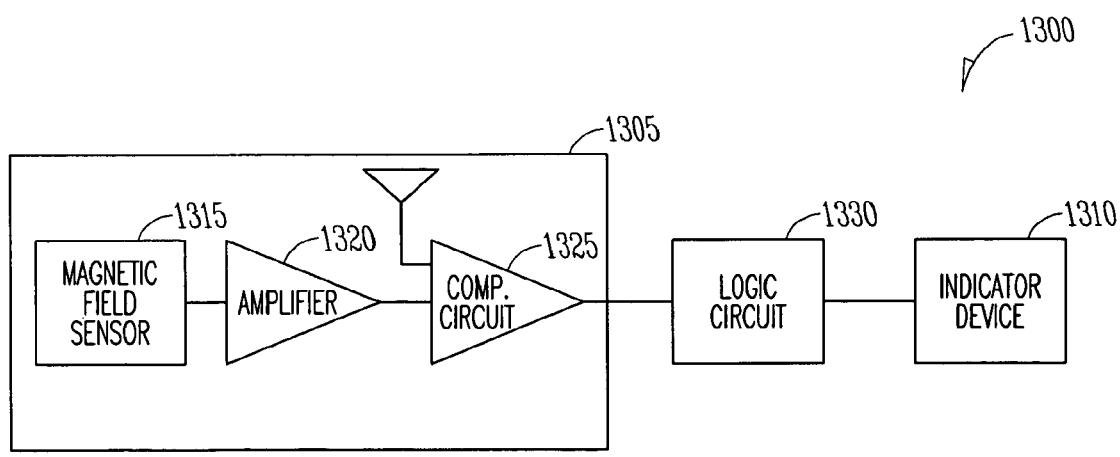
FIG. 13 is a block diagram of an implant detector device.

FIG. 13 is a block diagram of a lacrimal implant detector device 1300. The detector device 1300 detects an implanted punctum plug or other ocular implant. The detector device 1300 includes a magnetic field detector circuit 1305 and an indicator device 1310. The indicator device 1310 provides an indication upon detection of the magnetic field of the lacrimal implant to a user or automated process. The magnetic field detector circuit 1305 includes a magnetic field sensor 1315. In certain embodiments, the magnetic field sensor 1315 is a Hall Effect sensor. In certain embodiments, the magnetic field detection circuit 1305 includes an amplifier circuit 1320 to amplify a voltage output from the magnetic field sensor 1315.

In some embodiments, the magnetic field detector circuit 1305 includes a comparison circuit 1325 communicatively coupled to the magnetic field detection circuit. The communicative coupling allows the magnetic field sensor 1315 to communicate electrical signals with the comparison circuit 1325 even though there may be intervening circuitry (e.g., an amplifier circuit 1320). The comparison circuit 1325 provides an electrical signal to the indicator device 1310 when a voltage at an output of the magnetic field sensor 1315 exceeds a first threshold value. The magnetic field detector circuit 1305 may include a logic circuit (e.g., a flip-flop circuit or a latch) to capture a change in output from the comparison circuit indicating the presence of the magnetic field of the punctum plug.

In some embodiments, the comparison circuit 1325 provides the electrical signal to the indicator device 1310 when a voltage at the output of the magnetic field sensor 1315 exceeds the first threshold value and is less than a second threshold value.

Figure 14:
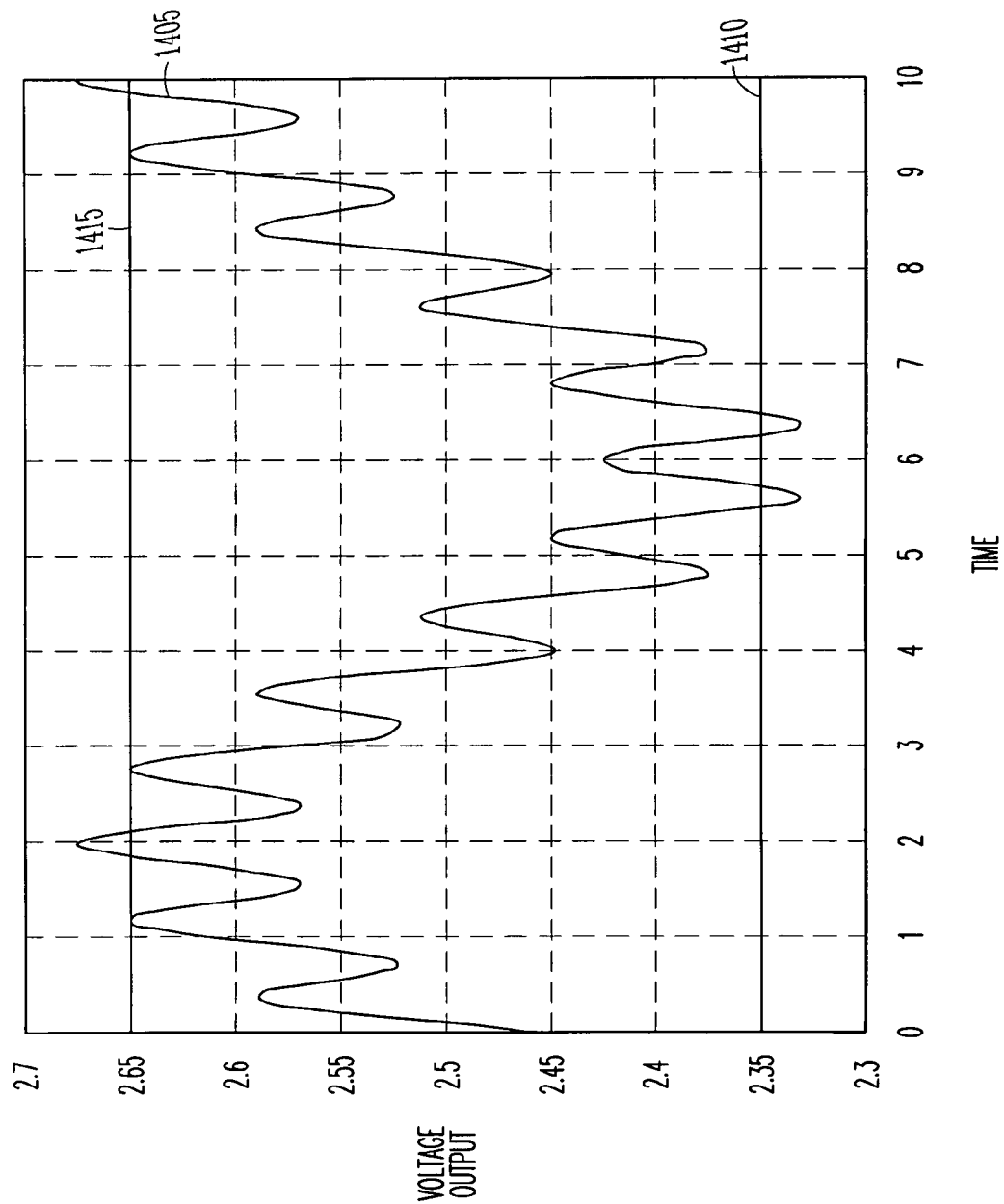
FIG. 14 shows a representation of an embodiment of a signal output from a Hall Effect sensor after amplification.

FIG. 14 shows a representation of an example of a signal 1405 output from a Hall Effect sensor after amplification. The comparison circuit 1325 provides an electrical signal to the indicator device 1310 when the signal 1405 exceeds the first threshold value 1410 (2.35V in the example) and is less than the second threshold value 1415 (2.65V). Returning to FIG. 13, the detector device 1300 may include a logic circuit 1330 (e.g., a flip-flop circuit or a latch). The logic circuit 1330 stores the state (high or low) of the electrical signal from the comparison circuit 1325.

In some embodiments, the indicator device 1310 includes a speaker or transducer. The indicator device 1310 provides an audible indication when the magnetic field detection circuit 1305 indicates the presence of the magnetic field of the punctum plug. In some embodiments, the indicator device 1310 includes a light emitting diode (LED) or display, and provides a visual indication upon detection of the magnetic field.

As shown in FIG. 5, the implant body 300 may include a cavity 340 extending inward into the plug body from an end of the plug body 300. The cavity 340 is shaped and sized to receive an implant core 510, or at least a portion of the implant core. The implant core 510 includes a sustained release ocular agent, such as to provide therapy to an eye. In some embodiments, the ocular agent includes a drug. The amount of agent in the plug core 510 is sufficient for sustained release to an eye over time.

Ferromagnetic material may be disposed in the implant core 510. The ferromagnetic material of the implant core 510 retains ferromagnetic properties after removal of an externally applied magnetic field. In some embodiments, ferromagnetic material is disposed in both the implant body and in the implant core 510 to provide a stronger magnetic field. Detecting the lacrimal implant 500 may help determine that the therapeutic agent is still present and being provided by the implant 500.

In some embodiments, a magnetic field is induced in the implant core 510 before insertion into the implant body 500, and in some embodiments, the magnetic field is induced after the implant core 510 is inside the implant body 500. In some embodiments, the outer part of the implant core 510 includes a sheath to house the agent. The ferromagnetic material is disposed within the sheath.

Figure 15:
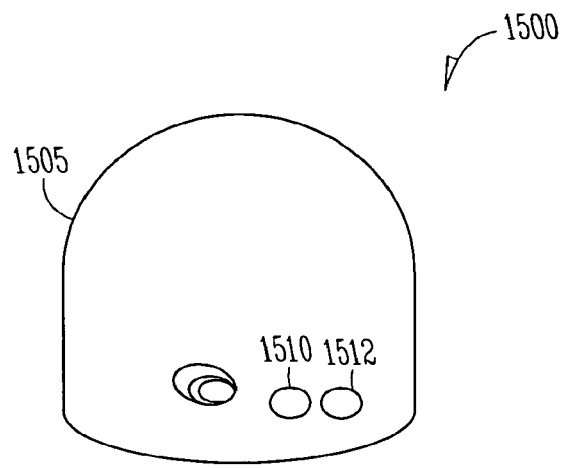
FIG. 15 is an illustration of an embodiment of a housing of an implant detector device.

FIG. 15 is an illustration of an embodiment of a housing 1505 of a lacrimal implant detector device 1500. The housing 1505 is shape of a cup and is sized to fit over an eye of a subject. The magnetic field sensor is arranged within the housing 1505 to detect the magnetic field of the lacrimal implant when the detector device 1500 is positioned over the eye. The detector device 1500 may include two LEDs 1510, 1512. The first LED 1510 is illuminated when the magnetic field of the lacrimal implant is detected. The second LED is illuminated when no magnetic field is detected. The LEDs may be different colors. For example, the first LED 1510 may be a green LED and the second LED 1515 may be a red LED.

Figure 16:
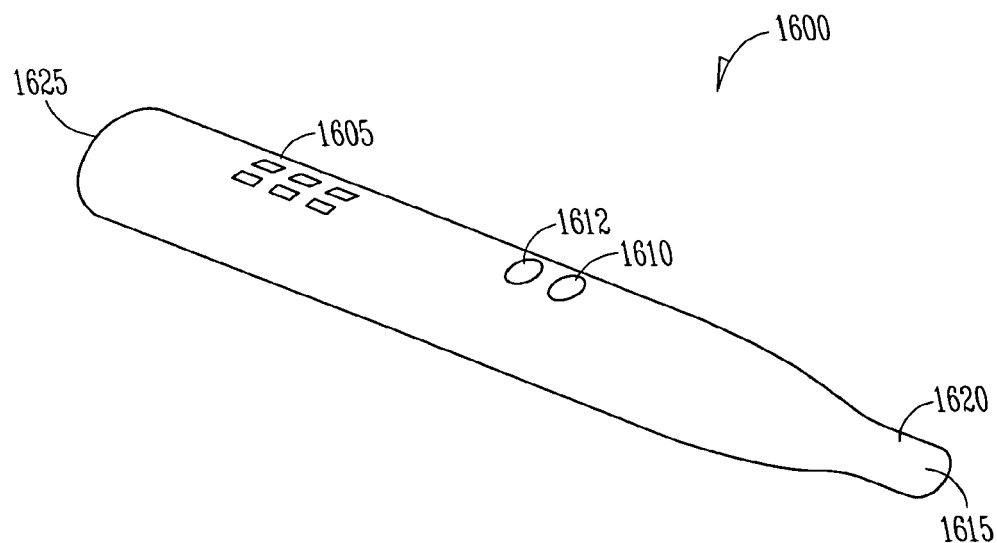
FIG. 16 is an illustration of another embodiment of a housing of an implant detector device.

FIG. 16 is an illustration of another embodiment of a housing 1605 of a lacrimal implant detector device 1600. This housing 1605 is elongate and has a proximal end 1620 and a distal end 1625. The magnetic field sensor 1615 is arranged near the proximal end 1620. This allows the lacrimal implant detection device 1600 to be held in the hand and used as a wand. LEDs 1610, 1612 are positioned at a point distal from the magnetic field sensor 1615 to allow the user to see the visual indication of whether the lacrimal implant is detected while the wand is held near the eye.

Figure 17:
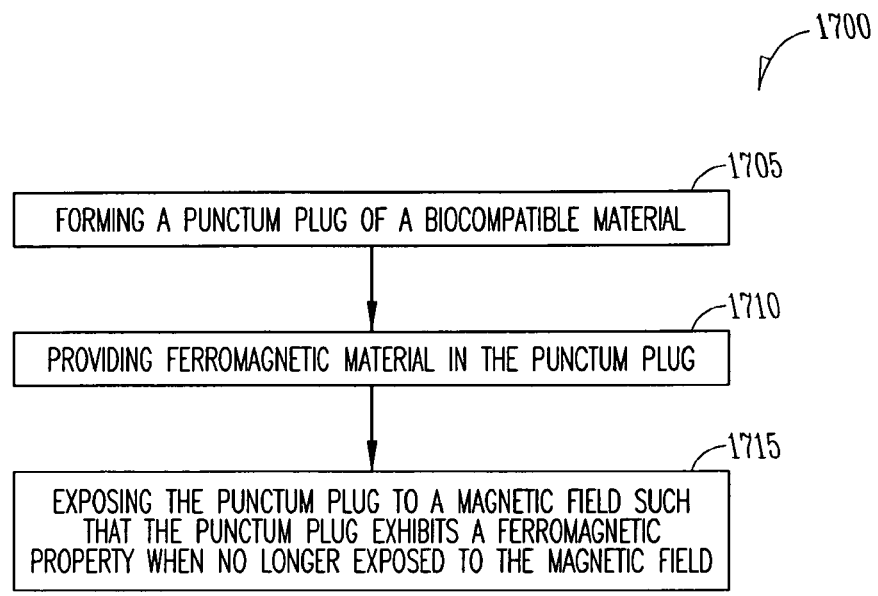
FIG. 17 is a flow diagram of another embodiment of method of making a device detectable lacrimal implant.

FIG. 17 is a flow diagram of a method of 1700 making a device-detectable lacrimal implant. At block 1705, a lacrimal implant, such as a punctum plug, is formed of a biocompatible material. At block 1710, ferromagnetic material is provided in the punctum plug. In certain embodiments, the ferromagnetic material is disposed in the biocompatible material. In certain embodiments, the ferromagnetic material is provided in an implant core within a cavity formed in a body of the punctum plug. In certain embodiments, the implant core includes a sheath to house an ocular agent and the ferromagnetic material is included in the sheath. In certain embodiments, the ferromagnetic material is provided in both the biocompatible material of the plug body and is provided in the plug core. At block 1715 the punctum plug is exposed to a magnetic field such that the lacrimal implant exhibits ferromagnetic properties when no longer exposed to the magnetic field.

The device-detectable lacrimal implant can be used to in a method of treating an eye disorder. In such a method, a lacrimal implant with the ferromagnetic material is inserted into at least one lacrimal punctum of the subject. A supply of a therapeutic agent is disposed in the implant core to provide sustained release of the agent. In certain embodiments, the agent is used to treat glaucoma, such as one or both of ocular hypertension and primary open angle glaucoma. The ferromagnetic property of the inserted lacrimal implant is detected with a lacrimal implant detector device.

If the detection device includes an electrically conductable material, impedance sensing can be used for lacrimal implant detection. Examples of electrically conductable material include, among other things, steel, silver, aluminum, and gold. The electrically conductive material may be provided as particles within the biocompatible material.

If the lacrimal implant includes an agent in the punctum plug body, particles of electrically conductive material and the agent may be disposed within the plug body. The lacrimal implant may include a sheath on the outer surface of the lacrimal implant that allows the agent to leach out from the implant but retains the electrically conductive particles.

In some embodiments, the lacrimal implant includes an implant core as shown in FIG. 5, and the electrically conductive material is included in the implant core. The electrically conductive material may be within the implant core or at the surface of the implant core, such as by including the electrically conductive material within a sheath used to house the therapeutic agent.

Figure 18:
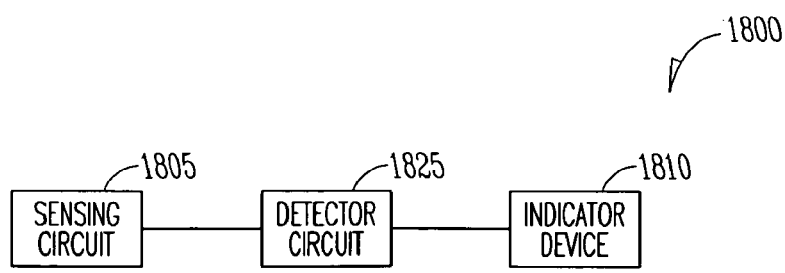
FIG. 18 is a block diagram of another embodiment of a device to detect an implant.

FIG. 18 is a block diagram of another embodiment of a device 1800 to detect a lacrimal implant. The lacrimal implant detector device 1800 includes a sensing circuit 1805, a detector circuit 1825, and an indicator device 1810. The sensing circuit 1805 includes an inductance and/or a capacitance that gives the sensing circuit 1805 a characteristic impedance. The impedance gives the sensing circuit a natural response frequency at which it operates. For example, the sensing circuit may be a tank circuit that oscillates at this frequency. When the sensing circuit 1805 is at or near the lacrimal implant, the electrically conductive material changes the characteristic impedance of the sensing circuit 1805, causing a shift in the natural frequency.

If the characteristic impedance of the sensing circuit 1805 is formed by one or more inductors, the conductive material disturbs the characteristic inductance of the sensing circuit 1805 to cause the shift in frequency. If the sensing circuit 1805 is formed by one or more capacitors, the proximity of the lacrimal implant changes the dielectric of the capacitance to cause the shift in frequency. This may be due to the dielectric of the material (e.g., aluminum) or from water included in the biocompatible material.

The detection circuit 1825 detects the change in characteristic impedance (e.g., by detecting a shift in the natural frequency). If a change is detected, the detector circuit 1825 provides an indication of the change to the indicator device 1810. The indicator device 1810 provides one or more of an audible indication or a visual indication upon detection of the change in the characteristic impedance due to the electrical conductivity of the lacrimal implant.

Figure 19:
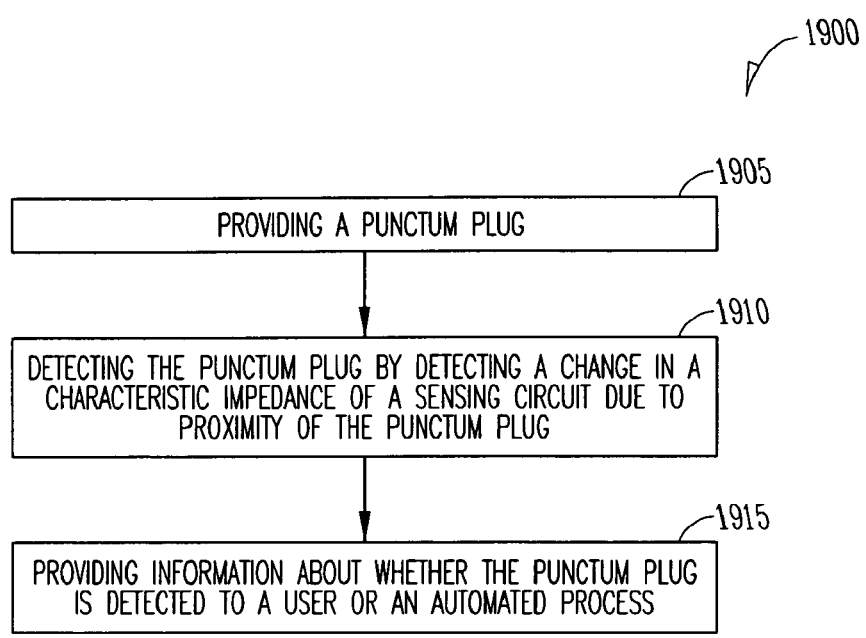
FIG. 19 is a flow diagram of a method of detecting an implant with a detector device.

FIG. 19 is a flow diagram of a method 1200 of detecting a lacrimal implant with a detector device. At block 1905, a lacrimal implant, such as a punctum plug, is provided. At block 1910, the punctum plug is detected by detecting a change in a characteristic impedance of a sensing circuit due to proximity of the punctum plug. In some embodiments, the detected change in characteristic impedance is a detected shift in a natural response frequency of the sensing circuit. Thus, the device may detect the lacrimal implant without contacting the punctum plug. The change in impedance seen at the sensing circuit is due to generated electric fields interacting with the lacrimal implant.

In certain embodiments, the device-detectable lacrimal implant includes electrically conductive material disposed in the biocompatible material of the lacrimal implant. In certain embodiments, a cavity is provided within a body of the lacrimal implant. An implant core is provided within the cavity that is shaped and configured to provide sustained release of an agent. The electrically conductive material may be provided in the implant core. In certain embodiments, the implant core includes a sheath to house the agent, and the electrically conductive material is included in the sheath. In certain embodiments, the electrically conductive material is provided in both the biocompatible material of the implant body and in the implant core.

At block 1915, information is provided to a user or automated process about whether the lacrimal implant is detected. In some embodiments, one or more of a visual or audible indication is provided to a user. In some embodiments, an indication is transmitted to an automated process of a second device.

The device-detectable lacrimal implant can be used in a method to treat an eye disorder. In such a method, a device-detectable lacrimal implant is inserted into at least one lacrimal punctum of a subject. The lacrimal implant includes a supply of an agent in the implant core to provide sustained release of the agent. In certain embodiments, the agent treats a glaucoma disease, such as one or both of ocular hypertension and primary open angle glaucoma. The lacrimal implant is detected by detecting a change in the characteristic impedance of a sensing circuit due to proximity of the lacrimal implant to the sensing circuit.

Figure 20:
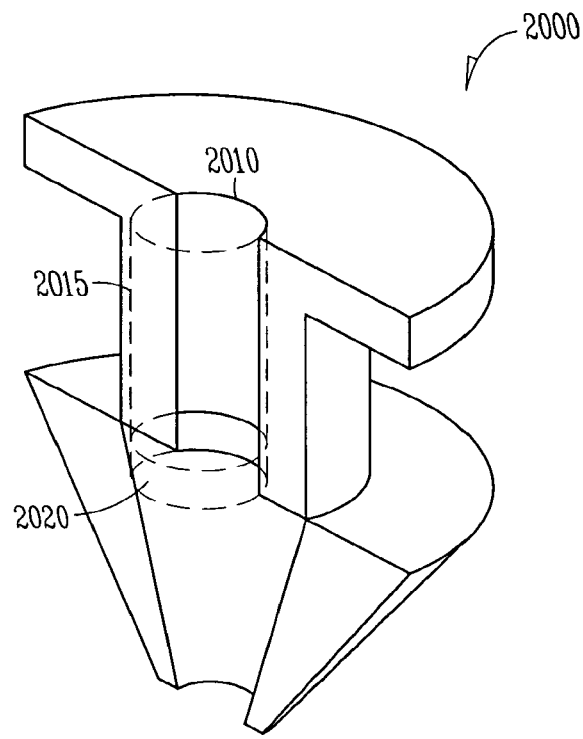
FIG. 20 shows an illustration of another embodiment of a lacrimal implant.

Detection devices may have properties to make the lacrimal implant optically detectable by a detector device. FIG. 20 shows an illustration of another embodiment of a lacrimal implant 2000, such as a punctum plug. The lacrimal implant 2000 includes an implant body 2005 of biocompatible material. The implant body 2005 includes a cavity 2010 extending inward into the implant body 2005 from an end of the implant body. The lacrimal implant 2000 includes an implant core 2015 sized and configured to provide sustained release of an agent into an eye. The implant core 2015 is carried within the cavity 2010 of the implant body, and the implant core 2015 includes a luminescent material 2020. In some embodiments, the agent is disposed in the biocompatible material of the implant body, and the luminescent material is included in the implant core.

In certain embodiments, the luminescent material 2020 includes a quantum dot. Quantum dots are semiconductor devices that receive light of a first wavelength range (e.g., a first color) and emit light of a different wavelength range (e.g., a second color). Generally, larger quantum dots work with in a lower frequency spectrum. For example, a larger quantum dot emits energy more towards the red (lower frequency) spectrum and smaller dots emit energy more towards the blue (higher frequency) spectrum.

Figure 21:
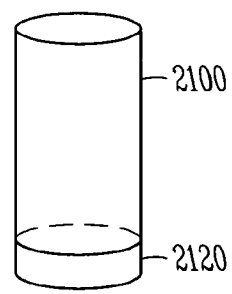
FIG. 21 shows an illustration of a sheath of a lacrimal implant core.

In some embodiments, the implant core 2015 includes a sheath to house the agent. FIG. 21 shows an illustration of a sheath 2100 of the implant core. The sheath 2100 may contain the luminescent material. The FIG. shows a representation of quantum dots 2120 included at the bottom of the sheath 2100. The agent is released through the opening at the top of the sheath 2100. Because quantum dots may be unstable at elevated temperatures, placing the quantum dot in the plug core may enhance quantum dot stability.

Figure 22:
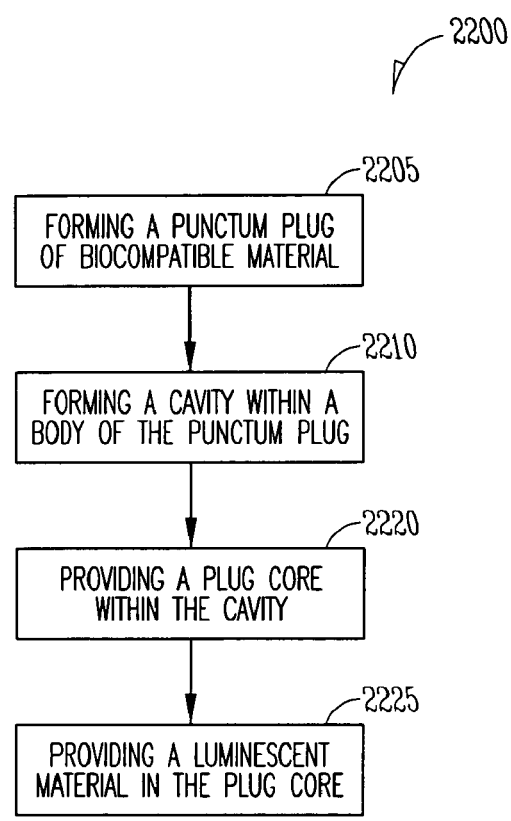
FIG. 22 is a flow diagram of another embodiment of a method of making a device detectable lacrimal implant.

FIG. 22 is a flow diagram of another embodiment of a method 2200 of making a device detectable lacrimal implant, such as a punctum plug. At block 2205, a punctum plug is formed of biocompatible material. At block 2210, a cavity is formed within a body of the punctum plug. At block 2215, a plug core is provided within the cavity. The plug core is sized and configured to provide sustained release of an agent into an eye. At block 2220, luminescent material is provided in the plug core.

A lacrimal implant detector device then detects the luminescent material 2020 of the lacrimal implant of FIG. 20. The detector device and the lacrimal implant 2000 form a system to provide sustained delivery of a therapeutic agent over time via a medical device insertable into the eye and to monitor the therapy by verifying the medical device continues to be present and delivering the agent.

The luminescent (e.g., a quantum dot) of the lacrimal implant 2000 is stimulated with a light source. The luminescent absorbs a higher power/lower wavelength form of light and converts the incident light into a lower power/higher wavelength form of light which is emitted. The lacrimal implant 2000 is detected when the expected higher wavelength form of light is detected.

Figure 23:
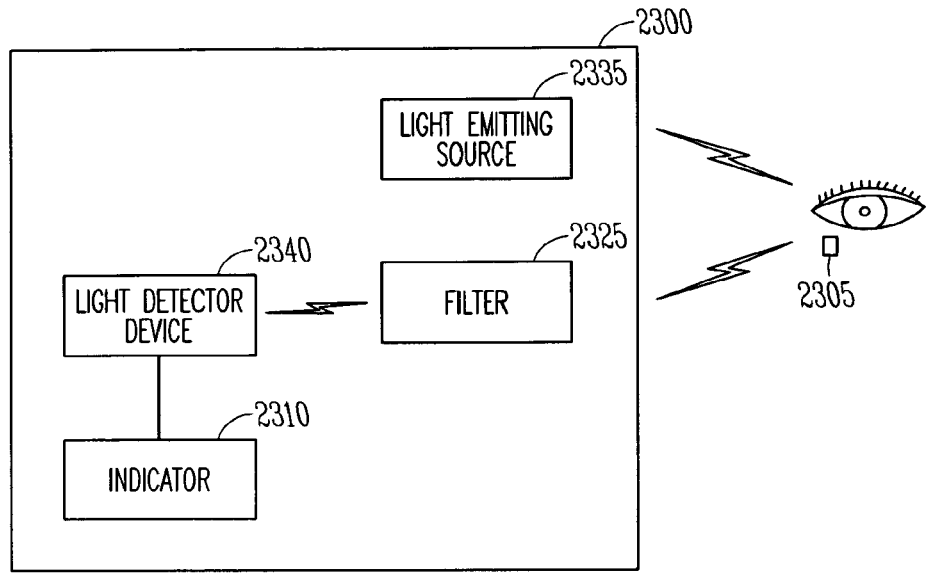
FIG. 23 is a block diagram of another embodiment of an implant detector device.

FIG. 23 is a block diagram of another embodiment of a lacrimal implant detector device 2300. The detector device 2300 includes a light emitting source 2335 to provide incident light to the nearby lacrimal implant 2305, an optical filter 2325, and a light detector device 2340. In some embodiments, the light emitting source 2335 includes a light emitting diode (LED). The optical filter 2325 is configured to pass light of a specified wavelength range reflected from a luminescent material of the lacrimal implant 2305. The light detector device 2340 is configured to receive the light passed by the optical filter 2325 and to produce a responsive electrical signal when sufficient light is received to indicate proximity of the lacrimal implant 2305. In some embodiments, the light detector device 2340 includes a photodiode to convert the energy passed by the optical filter 2325 into an electrical signal.

The light emitting source 2335 provides incident light having a first wavelength range and the luminescent material reflects the incident light in a second wavelength range. In some embodiments, the first wavelength range corresponds to a first color of light and the second wavelength range corresponds to a second color of light. For example, if the luminescent material includes quantum dots, the light emitting source 2335 may provide incident light in a blue spectrum (e.g., a blue LED) and the luminescent material reflects the incident light in a green spectrum which is passed by the optical filter 2325 and detected by the light detector device 2340. The photoexcitation behavior of the quantum dots exhibits a discrete interval of time between the absorption and the emission of light energy. This interval of time is on the order of 20 nanoseconds (ns).

In some embodiments, the incident and emitted light are both in the infrared or near-infrared spectrum. The light emitting source 2335 provides incident light of a first wavelength range in an infrared spectrum, and the luminescent material reflects the incident light in a different second wavelength range of the infrared spectrum. The shift in energy between the incident and emitted light is greater for the infrared spectrum than for the visible spectrum of light. This greater separation in wavelength between the incident and emitted light may make the filteringand detection process easier. Additionally, infrared light is not seen by an unaided eye. This makes the detection process more comfortable for the patient because bright visible light would not be shined into the patient's eye.

The detector device 2300 includes an indicator 2310 to provide a user indication of implant detection upon receiving the electrical signal from the light detector device 2340. In some embodiments, the indicator 2310 provides a visual indication and/or an audible indication.

Figure 24:
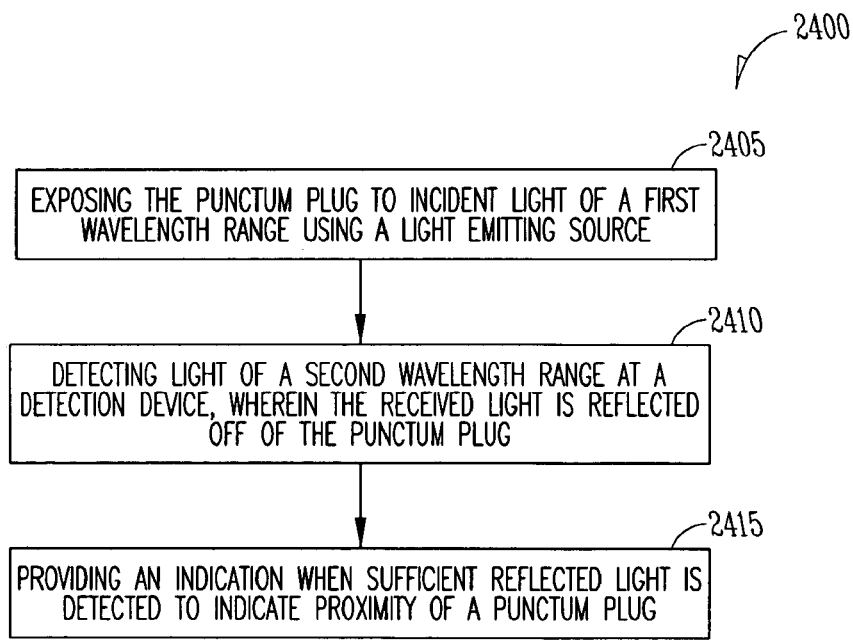
FIG. 24 is a flow diagram of another embodiment of a method of detecting a lacrimal implant.

FIG. 24 is a flow diagram of another embodiment of a method 2400 of detecting a lacrimal implant, such as a punctum plug. At block 2405, the punctum plug is exposed to incident light of a first wavelength range using a light emitting source. In some embodiments, the incident light is from a visible light spectra LED having a color corresponding to a wavelength within the first range.

At block 2410, light of a second wavelength range is detected using a detection device, wherein the received light is reflected off of the punctum plug. Broader spectrum white light may swamp the light detection. In some embodiments, the spectral range of the incident light is in the green light spectrum, and the spectral range of the reflected light is in the blue light spectrum. An isolation chamber may be useful to block out unwanted light from outside the relevant spectral ranges. In some embodiments, the incident light has a first wavelength range of an infrared spectrum, and the detected light has a second wavelength range of the infrared spectrum.

At block 2415, an indication is provided when sufficient reflected light is detected to indicate the proximity of the punctum plug. In some embodiments, a visual and/or audible indication is provided to a user. In some embodiments, an indication signal is communicated to an automated process of a second device. Such a device-detectable lacrimal implant may be used to treat an eye disorder. The lacrimal implant may include a supply of an agent in the plug core to provide sustained release of the agent. In certain embodiments, the agent treats a glaucoma disease.

Figure 25:
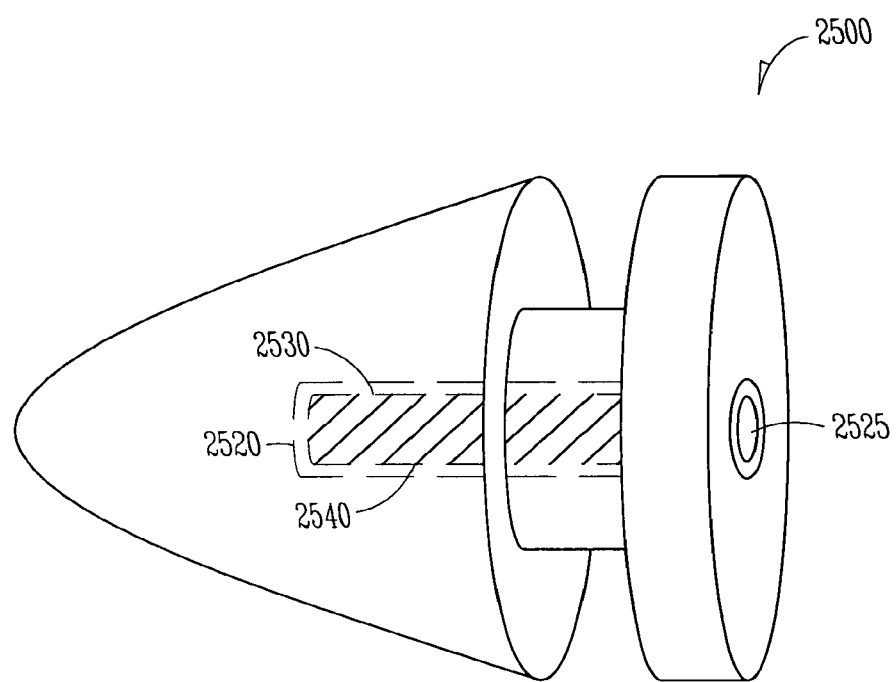
FIG. 25 shows an illustration of another embodiment of a lacrimal implant.

FIG. 25 shows an illustration of another embodiment of a lacrimal implant 2500. The implant core 2525 in the cavity 2520 includes an optical contrast material 2540 configured to optically distinguish the lacrimal implant from a region of an eye. The optical contrast material may include a pigment or a dye. In some embodiments, the optical contrast material is disposed on the surface of the implant core 2525. In some embodiments, the implant core includes a sheath 2530 to house an agent for sustained release, and the optical contrast material 2540 is disposed on the sheath 2530 that houses the agent.

To detect the lacrimal implant, an image of the region of the lacrimal punctum region of the eye is obtained, such as by using digital camera. An image processing algorithm is then used to locate a region of deeper contrast in the image. Because the depth focus of the image sensor may not be automatically and accurately set, the lacrimal implant will be determined to be in place according to some degree of probability. Obtaining an image of a region below the surface and potentially submerged in lacrimal canaliculus may be difficult. One way to obtain the image is to filter light around the spectral band of 600 to 1300 nanometers (nm). This may filter out intervening forms of tissue between the image sensor and the lacrimal implant.

Figure 26:
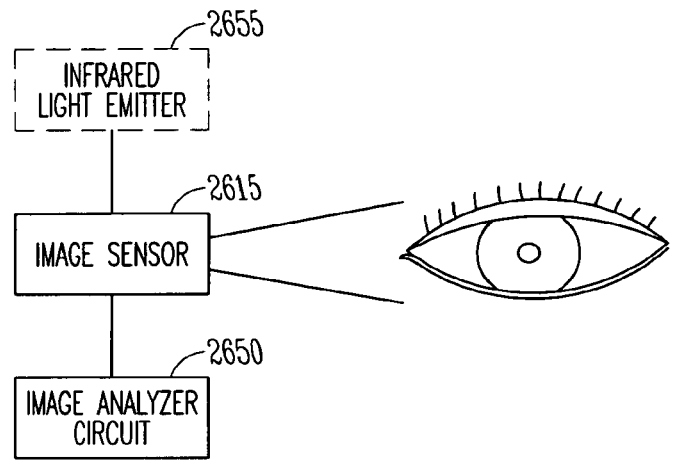
FIG. 26 is a block diagram of another embodiment of an implant detector device.

FIG. 26 is a block diagram of another embodiment of a lacrimal implant detector device 2600. The detector device 2600 includes an image sensor 2615 to obtain an image of at least a portion of an eye (e.g., the lacrimal punctum region). The lacrimal implant detection device 2600 also includes an image analyzer circuit 2650. The image analyzer circuit 2650 is configured to detect a location of an image portion having an image contrast that exceeds the image contrast in other areas of the image. Thus, if the lacrimal implant is present, the optical contrast of the lacrimal implant will exceed the contrast elsewhere in the image by a threshold image contrast value. The image analyzer circuit 2650 will detect the optical contrast and provide an indication of whether an image of portion of a lacrimal implant is in the image to a user or automated process.

In some embodiments, the image analyzer circuit 2650 includes a processor (e.g., a microprocessor) performing instructions to implement an image processing algorithm. In some embodiments, the image sensor 2615 is a digital image sensor included in a camera, and the detector device 2600 may include a memory to store the image for processing by the image analyzer circuit 2650. In some embodiments, the image analyzer circuit 2650 is included in the digital camera. In certain embodiments, the image analyzer circuit 2650 is included in a second device.

It may be difficult to obtain an image of the region of interest due to intervening tissue. In some embodiments, the detector device 2600 includes an infrared light emitter 2655, and the image sensor 2615 includes an infrared image sensor.

Figure 27:
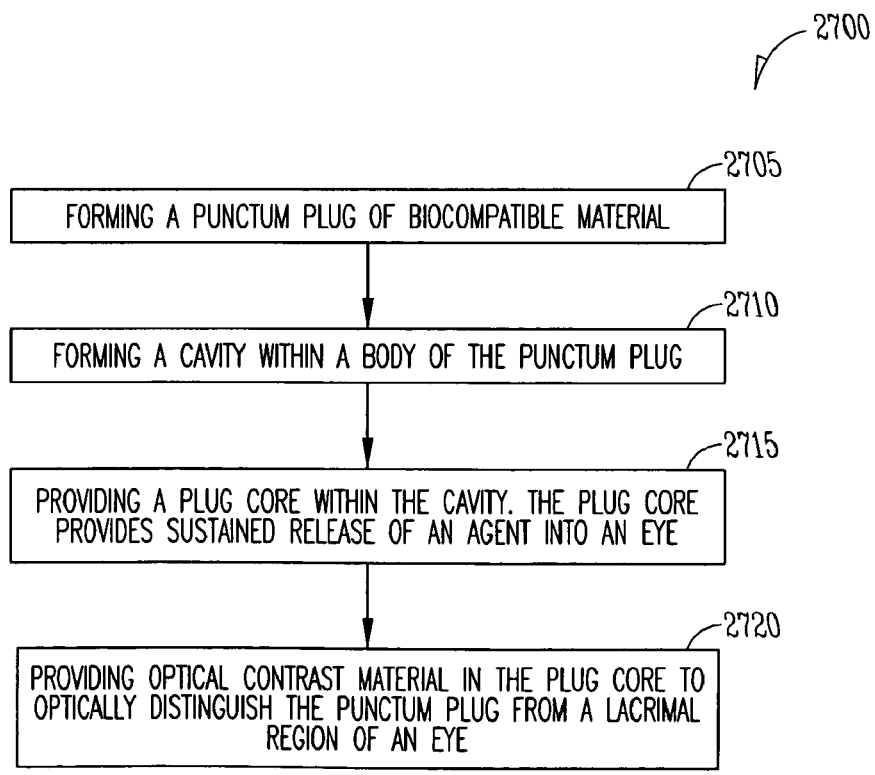
FIG. 27 is a flow diagram of another embodiment of a method of making a detectable implant.

FIG. 27 is a flow diagram of another embodiment of a method 2700 of making a device-detectable lacrimal implant. At block 2705, a lacrimal implant, such as a punctum plug, is formed of biocompatible material. At block 2710, a cavity is formed within a body of the punctum plug. At block 2715, a plug core is provided within the cavity. The plug core is sized and configured to provide sustained release of an agent into an eye. At block 2720, optical contrast material is provided in the plug core to optically distinguish the punctum plug from a lacrimal region of an eye. In some embodiments, providing optical contrast material in the plug core includes providing optical contrast material on the surface of the plug core. In some embodiments, providing a plug core includes providing a sheath in the plug core to house the agent. The optical contrast material in the plug core is included in the sheath.

The detectable lacrimal implant may be used in a method to treat an eye disorder. In such a method, the detectable lacrimal implant is inserted into at least one lacrimal punctum of the subject. The lacrimal implant has a supply of a sustained release agent disposed in the plug core. In certain embodiments, the agent is used to treat a glaucoma disease such as one or both of ocular hypertension and primary open angle glaucoma. To detect the lacrimal implant, an image of the lacrimal punctum region of the subject is obtained. The implant is detected when a location of an image portion having an image contrast that exceeds the image contrast in other areas of the image is detected.

If the implants disclosed herein include a therapeutic agent or drug supply, it is released at therapeutic levels to provide a desired treatment response when the implants disclosed above are implanted in a tissue or near the eye.

Therapeutic Agent Examples:

Several examples set forth above describe a plug core that provides sustained release of a therapeutic agent (or simply "agent"). An agent can comprise, among other things, a drug made from one or any combination of the following or their equivalents, derivatives or analogs, including, anti-glaucoma medications, (e.g. adrenergic agonists, adrenergic antagonists (beta blockers), carbonic anhydrase inhibitors (CAIs, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID or other analgesic and pain management compounds), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic, mydriatic or the like.

Example available agents include, but are not limited to, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Examples of such anti-inflammatory steroids contemplated for use with the present punctum plugs, include triamcinolone acetonide (generic name) and corticosteroids that include, for example, triamcinolone, dexamethasone, fluocinolone, cortisone, prednisolone, flumetholone, and derivatives thereof.); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil3; immunological drugs (such as vaccines and immune stimulants); hormonal agents (such as estrogens, -estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandins, prostaglandin precursors, including antiglaucoma drugs including beta-blockers such as Timolol, betaxolol, levobunolol, atenolol, and prostaglandin analogues such as bimatoprost, travoprost, latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

Additional agents that can be used with the present punctum plugs include, but are not limited to, drugs that have been approved under Section 505 of the United States Federal Food, Drug, and Cosmetic Act or under the Public Health Service Act, some of which can be found at the U.S. Food and Drug Administration (FDA) website http://www.accessdata.fda.gov/scripts/cder/drugsatfda/index. The present punctum plugs can also be used with drugs listed in the Orange Book, either in paper or in electronic form, which can be found at the FDA Orange Book website (http://www.fda.gov/cder/ob/)), that has or records the same date as, earlier date than, or later date than, the filing date of this patent document. For example, these drugs can include, among others, dorzolamide, olopatadine, travoprost, bimatoprost, cyclosporin, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, suprofenac, binoxan, patanol, dexamethasone/tobramycin combination, moxifloxacin, or acyclovir.

Examples of diseases or disorders that can be treated with above-listed agents include, but are not limited to, glaucoma, pre- and post-surgical ocular treatments, dry eye, anti-eye allergy, anti-infective, post-surgical inflammation or pain, respiration-related disorders, such as allergies, or inner ear disorders, such as dizziness or migraines. In some examples, the therapeutic agent can include a lubricant or a surfactant, for example a lubricant to treat dry eye. In other examples, the therapeutic agent can include an absorbent capable of absorbing tear from an eye.

Drug Supply Examples:

The drug supply can comprise one or more agents, and in some examples, one or more matrix materials to provide sustained release of the agents. The one or more agents can migrate from an exposed surface of the drug supply to the target tissue (e.g., ciliary muscles of an eye) based, at least in part, on a solubility of the agents in the matrix. The rate of migration of the agents from the exposed surface can also be related to the concentration of agents dissolved in the matrix. In some examples, the concentration of agents dissolved in the drug supply can be controlled to provide the desired release rate of the agents. In addition or in combination, the rate of migration of agents from the exposed surface can be related to one or more properties of the matrix in which the agents dissolve, such as the properties of a silicone matrix formulation. In some examples, the agents included in the drug supply can include liquid, solid, solid gel, solid crystalline, solid amorphous, solid particulate, or dissolved forms. In one such example, liquid Latanoprost droplets or solid Bimatoprost particles are dispersed in a silicone matrix.

The drug supply can comprise one or more biocompatible materials capable of providing a sustained release of the one or more agents. Although the drug supply is primarily discussed above with respect to an example comprising a matrix including a substantially non-biodegradable silicone matrix with dissolvable inclusions of the agents located therein, the drug supply can include other structures that provide sustained release of the agents, for example a biodegradable matrix, a porous drug supply, a liquid drug supply or a solid drug supply. A matrix that includes the agents can be formed from either biodegradable or non-biodegradable polymers. In some examples, a non-biodegradable drug supply can include silicone, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, Ill.; CONICHROME® from Carpenter Metals Corp., Wyomissing, Pa.). In some examples, a biodegradable drug supply can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some examples, the drug supply can comprise a hydrogel polymer.

The therapeutic agent or the drug supply is preferably released at a uniform rate, for example a rate that corresponds to zero order kinetics, although the therapeutic agent can be released at rates that correspond to other orders of reaction kinetics, for example first order. In many embodiments, the kinetic order of the reaction will vary from zero order to first order as the therapeutic agent is released. Thus, the therapeutic agent is released with a profile that corresponds to a range of kinetic orders that varies from about zero to about one. Ideally, the implant is removed before the rate at which the therapeutic agent is released changes significantly so as to provide uniform delivery of the therapeutic agent. As a uniform rate of delivery is desired, it may be desirable to remove and/or replace the implant before the reaction kinetics transition entirely to first order. In other embodiments, first or higher order release kinetics may be desirable during some or all of the treatment, so long as the therapeutic agent release profile remains within a safe and effective range. In some embodiments the cores may release the therapeutic agent at an effective rate for the period of 1 week to 5 years, more particularly in the range of 3-24 months. As pointed out above, in some embodiments it may be desirable for the detection agent and therapeutic agent to have similar release rates, for example the detection agent will indicate the continued release of the therapeutic agent. In other embodiments, it may be desirable for the detection agent and therapeutic agent to have different release rates, for example, the detection agent is released to let the patient know when the therapeutic agent is done releasing and to remove or change the implant.

The present invention is meant to embody all implants or devices which are implanted into the eye-lid canalicular puncta of the nasolacrimal system. The implants or devices include a detection device to let the patient know if the implant or device is in place, and in some embodiments, if the implant or device is still functioning properly, such as still delivering the therapeutic agent or drug.

Depending on the desired therapy, the some of the implants could be oriented in the punctal canal to deliver the drug either to the tear lake and thus the eye, or to the nasolacrimal system and thus the body's systemic circulation. The drawings illustrate only a few of the embodiments of the implant of the invention.

Figures 28, 28A:
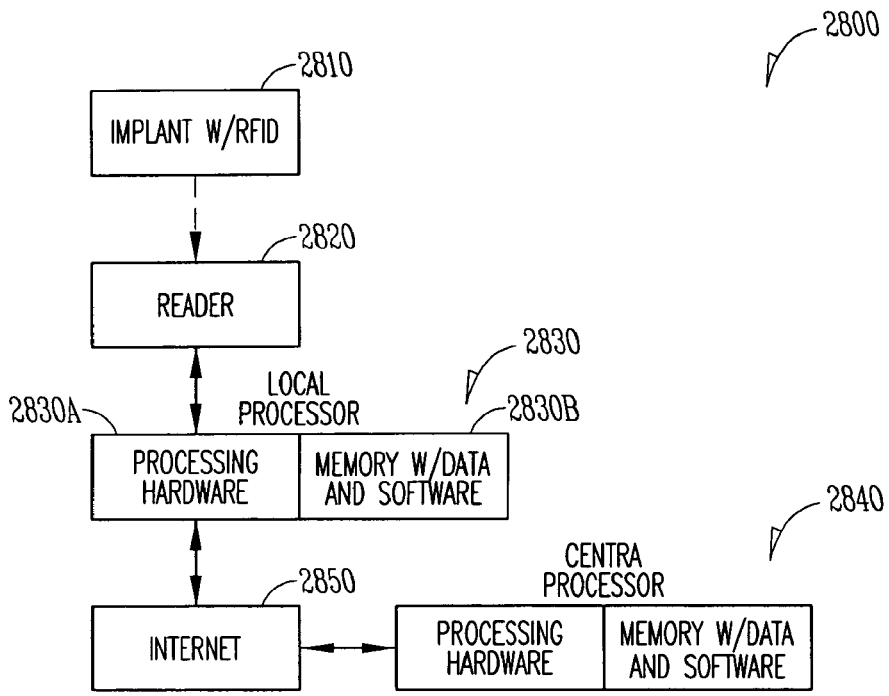
FIGS. 28 and 28A schematically illustrate an implant system for correlating implant data and tracking implant usage using radio frequency identification ("RFID") or other detection structures.

Referring now to FIG. 28, an implant data and tracking system 2800 generally facilitates correlation of implant data, tracking of implants, and the like. System typically includes a plurality of implants 2810 which may include one or more of the implant structures described herein. These implants will typically be suitable for ophthalmic use, but other system embodiments may find use for other medical indications and treatments with other drug delivery implants and the like.

Each implant associated with system 2800 may transmit a signal that is identifiable by a reader 2820. For example, the signal may be an RFID signal that allows identification of the implant as being a member a particular class or type of implants, as being a member of a particular population within a class or type of implants, and/or as being a particular unique implant. Alternative systems may employ light-based signals (including those signals generated using fluorescent signal tags released from the implant), magnetic signals, or the like. The reader will often comprise an off-the-shelf reader (such as a commercially available RFID reader, a commercially available spectral code reader, or the like), but may alternatively include a proprietary implant reader. The reader will transmit signals (typically electronically) to a processor 2830, allowing the processor to determine attributes of particular implant 2810 then being scanned or read.

Processor 2830 may include some or all of the components of a commercially available computer system. Processor 2830 will, for example, typically includes at least one processor circuit 2830A, which may communicate with a number of peripheral devices via a bus subsystem. These peripheral devices may include a memory system 2830B. The memory will typically include a tangible storage media embodying machine readable instructions for performing methods (including those described herein) and/or data. Memory 2830B may comprise a random access memory (RAM), a read only memory (ROM), a persistent (non-volatile) storage such as a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks including flash RAM. In some embodiments, processor 2830 will comprise a proprietary structure.

Some exemplary contents of memory 2830B or 2840 are schematically illustrated in FIG. 28A. In general, the memory may include a listing of individual implants, implant classes/types, and/or populations of implants. The listing of implants may, for each listing, include ID signal information to allow the processor to identify the implant, implant class, and/or implant population from the signals read by reader 2820. Optionally, the memory may also include (or allow access to) information regarding drugs or agents of the implants, dates of manufacture, shelf life, planned drug delivery spans for the implants, sizes of the implants, and/or the like. Particularly where the processor is used in or coupled to an implant location such as a doctor's office, the memory may also include information regarding the patient ID, the date of implantation, information regarding the presence of the implant at a follow-up visit, prior and/or subsequent patient health data (including indications of the efficacy of the implant), and/or the like. With access to this information, system 2800 may be used to help manage and/or track use of a large inventory of implants, many of which are implanted in a diverse patient population.

Simple systems might employ a single processor chip or integrated circuit running a monolithic computer program and packaged with a reader and an output in a small, hand-held unit. Alternatively, a wide variety of centralized or distributed data processing hardware and software architectures may be implemented. For example, a central processor 1040 may be located at (or be under the control of) an implant manufacturer or distributor, or a regulatory agency (such as the Food and Drug Administration in the United States). The central processor may be linked to each of a number of local clinical processors via a network such as the internet 2850 or the like. This distributed processor system may facilitate management of use and inventories of implants within a doctor's office, and also allow tracking of efficacy, adverse events, and the like throughout a range of different clinical settings. Hence, the functionality described herein may be implemented in a variety of software and/or hardware nodules distributed in different data processing structures and locations. For example, it will often be advantageous to provide readers (and often associated processors) at a plurality of differing doctor's offices, with each of the readers being able to determine attributes (such as the drug delivered by the implant, when the implant was implanted, and when the drug delivery period ends) of the implant. This may allow a patient with an implant to receive advice or treatment (such as replacement of the implant) at any clinical setting having the appropriate equipment, even when the patient does not have perfect information regarding the implant. The implant data system may also be incorporated into a range of alternative electronic record systems, optionally allowing automated messages being sent to a patient file or physician when the implant data is read and/or when the implant is implanted or removed using the Siemens SMS Medical Solutions system or the like.

EXAMPLE 1

Elution of Fluorescein and the Effect of Surfactant on Fluorescein Elution

Figure 29:
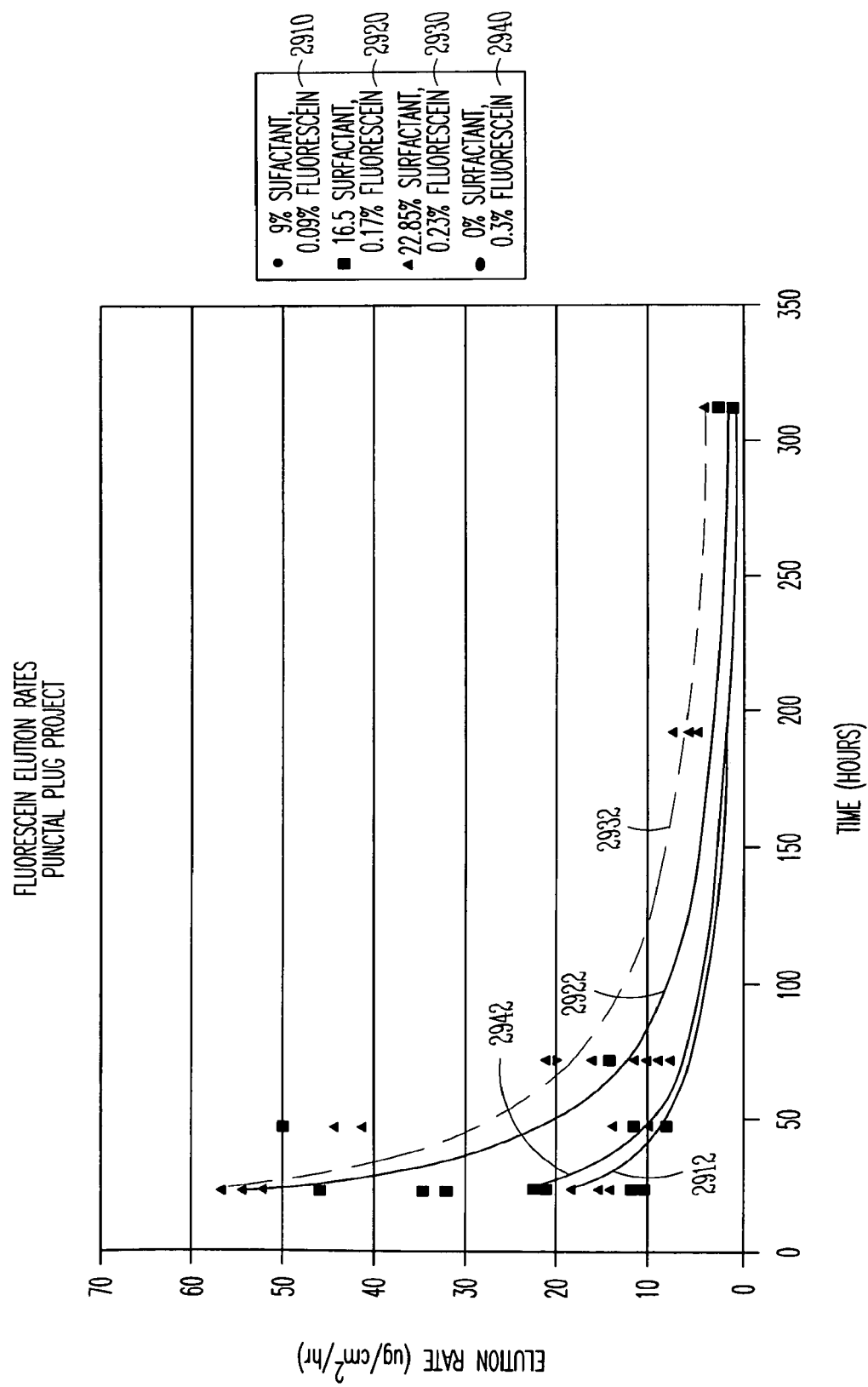
FIG. 29 shows the elution of fluorescein and the effect of surfactant on fluorescein elution, according to embodiments of the present invention.

FIG. 29 shows the elution of fluorescein and the effect of surfactant on fluorescein elution, according to embodiments of the present invention. The elution data for fluorescein show the flexibility of the above drug core and manufacturing processes for the sustained release of many therapeutic agents, including both water soluble and water insoluble therapeutic agents, and relatively low molecular weight and high molecular weight therapeutic agents. In some embodiments, a detection agent may comprise fluorescein eluted with a therapeutic agent, as described above. Fluorescein has a molecular mass of 332.32 g/mol, is soluble in water, and can serve as a model for the release water soluble therapeutic agents released from the eye. Work in relation with embodiments of the present invention indicates that molecular weight and solubility in water can each affect the release rate of the drug from the solid drug core matrix. For example, lower molecular weight may increase diffusion through the solid matrix material, i.e., through silicone, such that low molecular weight compounds may be released more quickly. Also, solubility in water can also effect the release rate of the drug, and in some instances increased water solubility of the drug may increase the rate of release from the solid drug core matrix, for example via transport from the solid matrix material to the bodily liquid, such as tear liquid. In accordance with these embodiments, therapeutic agents with higher molecular weight than fluorescein and with lower water solubility than fluorescein, for example cyclosporin and prostaglandins as shown above, may be released from the solid core at lower rates. Surfactants may also affect the rate of release of the therapeutic agent from the drug core into the surrounding bodily tissue and/or fluid, for example tear film fluid.

Each drug core tested comprised MED 4011 silicone. In one embodiments, a drug core formulation 2910 comprised 9% surfactant and 0.09% fluorescein. An exponential fit 2912 is shown for the elution rate of drug core formulation 2910. In another embodiment, a drug core formulation 2920 comprised 16.5% surfactant and 0.17% fluorescein. An exponential fit 2922 is shown for the elution rate of drug core formulation 2920. In another embodiment, a drug core formulation 2930 comprised 22.85% surfactant and 0.23% fluorescein. An exponential fit 2932 is shown for the elution rate of drug core formulation 2930. In an embodiment without surfactant, a drug core formulation 2940 comprised 0% surfactant and 0.3% fluorescein. An exponential fit 2942 is shown for the elution rate of drug core formulation 2940.

The drug cores were manufactured with key formulations comprising: Silicone Surfactant "190 Fluid" (Dow Corning); Surfactant Mix: "190 Fluid"+Fluorescein; Silicone (Nusil): MED 4011 Part A, MED 4011 Part B; Centrifuge Tubes; 3 mL Syringe; 20 ga. Needle; 0.031 inch inner diameter Teflon Tube; and Buffer.

Key parameters included: Prepare a mixture of 2.5 g of silicone surfactant and 0.025 g of fluorescein; Prepare silicone compositions of Nusil MED 4011 containing 3.5 g Part A and 0.37 g Part B (10:1 ratio); Prepare four (4) centrifuge tubes each with 0.5 g of silicone and varying surfactant mixture weights as follows: A. 0.05 g surfactant mix: 9% surfactant, 0.09% fluorescein; B. 0.1 g surfactant mix: 16.5% surfactant, 0.17% fluorescein; C. 0.15 surfactant mix: 22.85% surfactant, 0.23% fluorescein; D. 0.0015 g fluorescein: 0% surfactant, 0.3% fluorescein; Inject each of the four formulations into respective teflon tubes using the syringe and needle; Cure the injected tube at 140° C. for 45 minutes in the oven; Cut each tube into 3 pieces in length to 4 mm; and Immerse each cut piece into a centrifuge tube containing 0.3 mL of buffer Data collection comprised: Collect samples at time points 24, 48, 72, 192, and 312 hours; Submit each sample for UV spectrometry analysis; Convert each elution rate from μg/mL/hr to μg/cm$^2$/hr by using the dimensions of the teflon tube (4 mm length, 0.031 inch inner diameter); Plot data for elution rate vs. time to compare the rates of each surfactant mix formulation Analysis comprised fitting trendlines for each elution rate to an exponential curve, as shown in Table 1.

TABLE 1

Trendlines for each elution rate fit to exponential curves.

| Sample # | % Surfactant | % Fluorescein | R$^2$ | Trendline Equation |
|---|---|---|---|---|
| A | 9.0 | 0.09 | 0.9497 | $636.66x^{-1.1161}$ |
| B | 16.5 | 0.17 | 0.8785 | $4289.6x^{-1.3706}$ |
| C | 22.85 | 0.23 | 0.9554 | $1762.0x^{-1.0711}$ |
| D | 0 | 0.30 | 0.9478 | $1142.1x^{-1.2305}$ |

The trendline equations of table 1 indicate the following: The data fit experimental curves well with R$^2$ values of 0.8785 to 0.9554. The trendline equations show exponent coefficients of −1.0711 to −1.3706. Elution rates increased with increasing surfactant levels. Despite relatively similar amounts of fluorescein, there is a dramatic increase in elution rates between Samples C and D—this demonstrates that the addition of surfactant to the silicone matrix dramatically affects the elution rate of the water-soluble compound. The elution rate of Sample A is comparable to that of Sample D, even though Sample A contains only one-third the amount of fluorescein. This also demonstrates that the rate of elution can be affected by the addition of surfactant to the silicone matrix.

Although the trendline equation exponent coefficients of −1.0711 to −1.3706 are consistent with first order release, the data include an initial 48 hour period in which bolus release of fluorescein from the core is observed. Such an initial washout period of 2 to 3 days with high levels of the therapeutic agent delivered followed by a period of sustained release at therapeutic levels can be helpful in some embodiments, for example where elevated levels for a short period of time are tolerated and can lead to an accelerated effect on the eye. Work in relation with embodiments of the present invention suggests that after 48 hours the elution data can be closer to zero order, for example within a range from about zero order to about first order.

Figure 30:
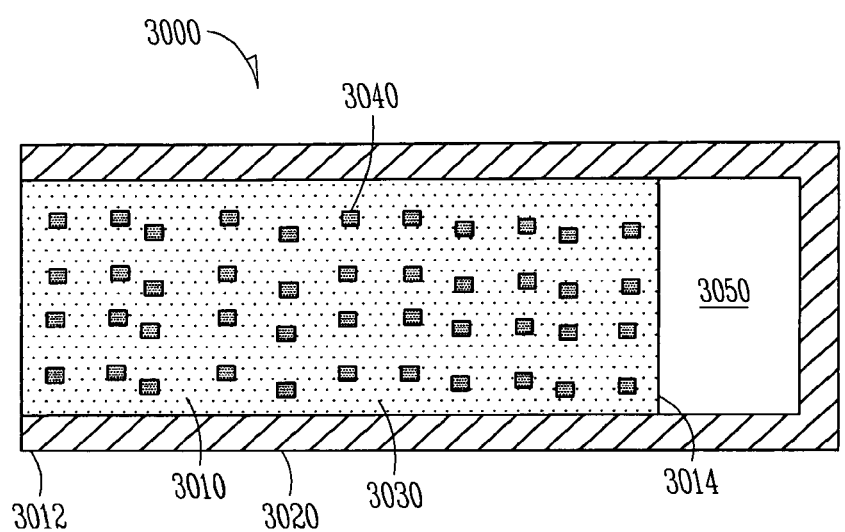
FIG. 30 shows a sectional view of an implant having a core with a therapeutic agent and a detection device, according to an embodiment of the present invention.

FIG. 30 shows a cross sectional view of a drug delivery implant 3000 having a therapeutic agent and a detection device 3050, according to embodiments of the present invention. Implant 3000 includes a core 3010 having a proximal end 3012 and a distal end 3014 having a detection agent therein. In the embodiment shown, the core 3010 also includes the therapeutic agent. The core 3010 comprises a matrix 3030 that contains inclusions 3040 of therapeutic agent. Inclusions 3040 may comprise a concentrated form of the therapeutic agents, for example a liquid or solid form of the therapeutic agents, and the therapeutic agents may over time dissolve into matrix 3030 of core 3010. Matrix 3030 can comprise a silicone matrix or the like, and the mixture of the detection agent and therapeutic agent within matrix 3030 can be non-homogeneous. The core 3010, matrix 3030, inclusions 3040 and therapeutic agents may include any core, matrix, inclusions and therapeutic agents described in the present application. In many embodiments, the non-homogenous mixture comprises a silicone matrix portion that is saturated with the detection agent and therapeutic agent and an inclusions portion comprising inclusions of the detection agent and therapeutic agent, such that the non-homogenous mixture comprises a multiphase non-homogenous mixture. In some embodiments, matrix 3030 encapsulates inclusions 3040 and inclusions 3040 may comprise microparticles having dimensions from about 1 μm to about 100 μm. The encapsulated inclusions dissolve into the surrounding solid matrix, for example silicone, that encapsulates the micro particles such that matrix 3030 is substantially saturated with the detection agent and therapeutic agent, while the detection agent and therapeutic agent are released from the core. The therapeutic agent is released at therapeutic levels to provide a desired treatment response when the implant 3000 is implanted in the body. The drug core may release the therapeutic agent at an effective rate for the period of 1 week to 5 years, more particularly in the range of 3-24 months. In some embodiments, the therapeutic level is less than a dose administered quantity or less or 5-10% of the dose administered quantity, typically being less than 10% and often being 5% or less than the dose administered quantity each day for an extended period of days. The dose administered quantity may be the oral dose or may be an injectable dose.

At the distal end 3014 of the core 3010 is the detection device 3050. The detection device 3050 may be any device that aids in the detection and/or identification of the implant 3000 when positioned within the body. In one embodiment, the detection device 3080 may include a detection signal allowing detection of the implant and/or identification of an attribute of the implant from among a plurality of alternative attributes of implants. In one example, the transmitting signal comprises a radio signal of a RFID chip capable of detection with an RFID detector, the signal comprising a radio signal identification signal. In other examples, the signal includes a magnetic signal from a material capable of detection with a magnetic detector, or an ultrasonically reflective material capable of detection with an ultrasonic detector.

Core 3010 and detector 3050 fits within a channel of a sheath body 3020. Sheath body 3020 is substantially impermeable to the therapeutic agent, so that the therapeutic agent is released from an exposed surface on the proximal end 3012 of core 3010 that is not covered with sheath body 3020. The detector 3050 may also be molded into the sheath body 3020.

The therapeutic agent used in the implant 3000 may be used for different treatment and conditions, and may include the therapeutic agents disclosed in U.S. application Ser. No. 11/695,537, titled "Drug Delivery Methods, Structures, and Compositions for Nasolacrimal Systems; U.S. application Ser. No. 11/695,545, titled "Nasolacrimal Drainage System Implants for Drug Therapy"; U.S. App. No. 60/871,867, titled "Drug Delivery Implants for Inhibition of Optical Defects"; U.S. App. No 60/970,709, titled "Nasolacrimal Drainage System with Implants for Drug Delivery", U.S. App. No. 60/970,820, titled "Multiple Drug Delivery Systems and Combinations of Drugs with Punctal Implants", the full disclosures of which are incorporated herein by reference.

Figure 31:
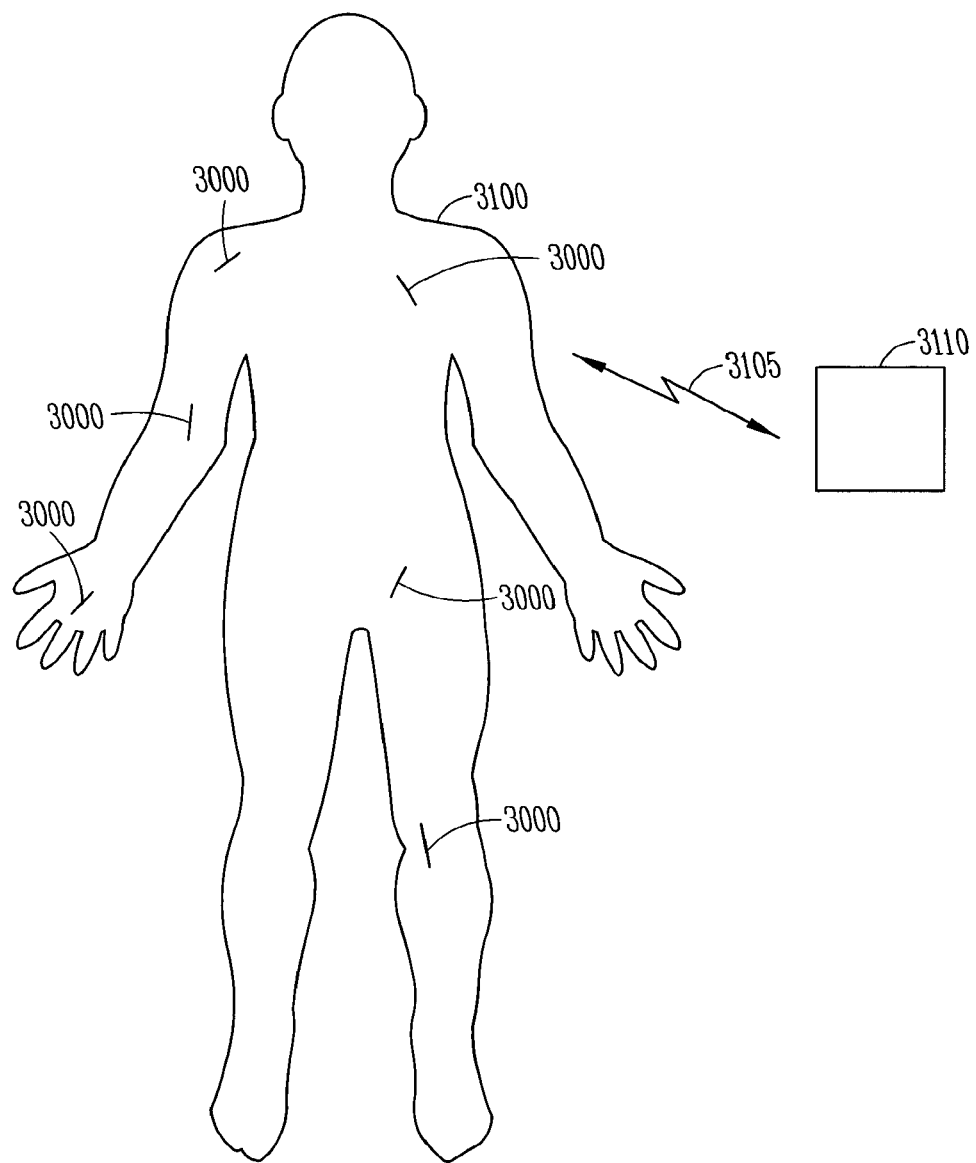
FIG. 31 shows one embodiment of a therapeutic implant to treat a body condition, the implant having a detection device.

FIG. 31 shows drug delivery therapeutic implants 3000 in a body 3100 to treat a body condition. The therapeutic implants 3000 are sustained release implants with a drug core containing a therapeutic agent, and a detector as discussed above. The therapeutic implant may be implanted by known means.

In use, the therapeutic implant 3000 is implanted in the body 3100, where a body fluid may contact the exposed surface of the drug core, releasing the therapeutic agent. Depending on the implant location, any body fluid proximate the therapeutic implant, such as blood, may contact the exposed surface, releasing the therapeutic agent from the implant. The therapeutic implant location may include body locations for local drug delivery to joints, such as proximate the shoulder, knee, elbow, finger, or a trauma location, or a tumor location, other locations, such as the abdomen, for general drug delivery. The therapeutic implant 3000 may include on or more retention elements known in the art to retain the therapeutic implant 3000 near a body location, such as the body locations listed above.

The detection device 3050 within the therapeutic implant 3000 can be detected and/or identified many different ways. For example, in some embodiments, the detection device 3050 may communicate 3105 with a detection system 3110 that can detect and/or identify the implant 3000. Detection system 3110 may include any or all of the features discussed with detection system 1065 and system 2800 above. For example, the detection system 3110 may include a RFID detection system to detect a RFID chip, a magnetic detector system to detect a magnetic material, an ultrasonic detector system to detect ultrasonically reflective material, or any other detection system described herein.

In one embodiment, the therapeutic implant 3000 is used in oncology, where a local therapeutic implant drug delivery could allow an extra benefit of treating a tumor site post surgically, and minimizing the collateral damage to the rest of the body. An example would be lumpectomy for breast tumor or surgical treatment of prostate cancer, where the therapeutic implant would be implanted near the cancer site. In fact any solid tumor would be a target, with the therapeutic implant being implanted near the tumor.

In joints, non-steroidal anti-inflammatory drugs (NSAIDs) may be used for the treatment of such things as osteoarthritis and rheumatoid arthritis. Delivery of NSAIDs locally would reduce the risk associated with systemic cox II inhibitors, such as gastrointestinal problems (problems in the stomach or intestine) the may include stomach ulcers or bleeding, and possibly life threatening perforations (rips or holes) in the wall of the stomach or intestine. In this embodiment, the therapeutic implant is positioned near the joint to deliver NSAIDs locally.

In another embodiment, a therapeutic implant may be used for localized delivery of multiple drugs to a trauma site, such as delivering an analgesic or an anti-infectives. While specific embodiments of the invention has been shown and described in detail to illustrate the application of the principles of the invention, it will be understood that the invention may be embodied otherwise without departing from such principles. For example, simple mechanical indicators could be used to provide information regarding the state of the implant (such as that the implant has been implanted for an intended treatment time or the like). For example, time-dependent erosion of a film may detectable alter the implant by changing a color or reflectiveness of a surface, allow release of a colored or fluorescing material, allow swelling of a material, or the like. A simple chemical or mechanical clock of the implant may begin running and/or stop running when the implant is implanted, allowing determination of the implant and/or desired removal date.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Some of the method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

What is claimed is:

1. A lacrimal implant for insertion into a lacrimal canaliculus of a patient comprising:
   a therapeutic agent and a contrast agent admixed with biocompatible material comprising a hydrogel polymer wherein the contrast agent is configured to optically distinguish the lacrimal implant from a region of an eye and wherein a release rate of the therapeutic agent and contrast agent are different.

2. The lacrimal implant of claim 1, wherein the contrast agent includes a material visible when illuminated with a 600-1300 nanometer light source.

3. The lacrimal implant of claim 1, wherein the contrast agent comprises a color material, a pigment, a luminescent material, or a dye.

4. The lacrimal implant of claim 1, wherein the therapeutic agent comprises travoprost, a non-steroidal anti-inflammatory agent (NSAID), anti-glaucoma drugs, prostaglandin analogues, a corticosteroid, an anti-inflammatory agent, an anti-allergy agent, antimicrobial agents, cycloplegic drugs, or mydriatic drugs.

5. The lacrimal implant of claim 1, wherein the contrast agent comprises fluorescein.

6. The lacrimal implant of claim 1, wherein the lacrimal implant is green.

7. The lacrimal implant of claim 1, wherein the therapeutic agent is travoprost.

8. The lacrimal implant of claim 1, wherein the therapeutic agent is dexamethasone.

9. The lacrimal implant of claim 1, wherein the therapeutic agent is an antimicrobial agent.

10. The lacrimal implant of claim 1, wherein the contrast agent comprises a material visible when illuminated with a visible light source.

11. The lacrimal implant of claim 1, wherein the biocompatible material is biodegradable.

12. The lacrimal implant of claim 1, wherein the biocompatible material comprises a biodegradable hydrogel polymer.

13. A lacrimal implant for insertion into a lacrimal canaliculus of a patient comprising:
   a therapeutic agent and a contrast agent admixed with a biodegradable material comprising a hydrogel polymer wherein the contrast agent is configured to optically distinguish the lacrimal implant from a region of an eye and wherein a release rate of the therapeutic agent and contrast agent are different.

14. The lacrimal implant of claim 13, wherein the contrast agent includes a material visible when illuminated with a 600-1300 nanometer light source.

15. The lacrimal implant of claim 13, wherein the contrast agent comprises a color material, a pigment, a luminescent material, or a dye.

16. The lacrimal implant of claim 13, wherein the therapeutic agent comprises travoprost, a non-steroidal anti-inflammatory agent (NSAID), anti-glaucoma drugs, prostaglandin analogues, a corticosteroid, an anti-inflammatory agent, an anti-allergy agent, antimicrobial agents, cycloplegic drugs, or mydriatic drugs.

17. The lacrimal implant of claim 13, wherein the contrast agent comprises fluorescein.

18. The lacrimal implant of claim 13, wherein the lacrimal implant is green.

19. The lacrimal implant of claim 13, wherein the therapeutic agent is travoprost.

20. The lacrimal implant of claim 13, wherein the therapeutic agent is dexamethasone.

21. The lacrimal implant of claim 13, wherein the therapeutic agent is an antimicrobial agent.

22. The lacrimal implant of claim 13, wherein the contrast agent comprises a material visible when illuminated with a visible light source.

23. The lacrimal implant of claim 13, wherein the biodegradable material comprises a biodegradable hydrogel polymer.

24. A lacrimal implant for insertion into a lacrimal canaliculus of a patient comprising:
   a therapeutic agent and a contrast agent admixed with a biodegradable hydrogel polymer wherein the contrast agent comprises a color material, a pigment, a luminescent material, or a dye, and wherein a release rate of the therapeutic agent and contrast agent are different.

25. The lacrimal implant of claim 24, wherein the contrast agent is visible when illuminated with a 600-1300 nanometer light source.

26. The lacrimal implant of claim 24, wherein the therapeutic agent comprises travoprost, a non-steroidal anti-inflammatory agent (NSAID), anti-glaucoma drugs, prostaglandin analogues, a corticosteroid, an anti-inflammatory agent, an anti-allergy agent, antimicrobial agents, cycloplegic drugs, or mydriatic drugs.

27. The lacrimal implant of claim 24, wherein the contrast agent comprises fluorescein.

28. The lacrimal implant of claim 24, wherein the lacrimal implant is green.

29. The lacrimal implant of claim 24, wherein the therapeutic agent is travoprost.

30. The lacrimal implant of claim 24, wherein the therapeutic agent is dexamethasone.

31. The lacrimal implant of claim 24, wherein the therapeutic agent is an antimicrobial agent.

32. The lacrimal implant of claim 24, wherein the contrast agent is visible when illuminated with a visible light source.

33. A lacrimal implant for insertion into a lacrimal canaliculus of a patient comprising:
   a therapeutic agent, a detection agent and hydrogel polymers that form a hydrogel matrix with the therapeutic agent and detection agent dispersed through the hydrogel matrix, wherein the shape of the lacrimal implant consists of a constant diameter cylinder, and wherein a release rate of the therapeutic agent and detection agent are different.

34. The lacrimal implant of claim 33, wherein the detection agent comprises a color material, a pigment, a luminescent material, or a dye.

35. The lacrimal implant of claim 33, wherein the therapeutic agent comprises travoprost, a non-steroidal anti-inflammatory agent (NSAID), anti-glaucoma drugs, prostaglandin analogues, a corticosteroid, an anti-inflammatory agent, an anti-allergy agent, antimicrobial agents, cycloplegic drugs, or mydriatic drugs.

36. The lacrimal implant of claim 33, wherein the detection agent comprises fluorescein.

37. The lacrimal implant of claim 33, wherein the lacrimal implant is green.

38. The lacrimal implant of claim 33, wherein the therapeutic agent is travoprost.

39. The lacrimal implant of claim 33, wherein the therapeutic agent is dexamethasone.

40. The lacrimal implant of claim 33, wherein the therapeutic agent is an antimicrobial agent.

41. The lacrimal implant of claim 34, wherein the detection agent comprises a material visible when illuminated with a visible light source.

42. A lacrimal implant for insertion into a lacrimal canaliculus of a patient comprising:
a therapeutic agent, fluorescein and hydrogel polymers that form a hydrogel matrix with the therapeutic agent and fluorescein dispersed through the hydrogel matrix, wherein the shape of the lacrimal implant consists of a constant diameter cylinder, and wherein a release rate of the therapeutic agent and the fluorescein are different.

43. The lacrimal implant of claim 42, wherein the therapeutic agent comprises travoprost, a non-steroidal anti-inflammatory agent (NSAID), anti-glaucoma drugs, prostaglandin analogues, a corticosteroid, an anti-inflammatory agent, an anti-allergy agent, antimicrobial agents, cycloplegic drugs, or mydriatic drugs.

44. The lacrimal implant of claim 42, wherein the therapeutic agent is travoprost.

45. The lacrimal implant of claim 42, wherein the therapeutic agent is dexamethasone.

46. The lacrimal implant of claim 42, wherein the therapeutic agent is an antimicrobial agent.

* * * * *